United States Patent [19]

Sauers

[11] Patent Number: 4,460,401

[45] Date of Patent: Jul. 17, 1984

[54] BENZENESULFONAMIDES AS HERBICIDES

[75] Inventor: Richard F. Sauers, Hockessin, Del.

[73] Assignee: E. I. Du Pont de Nemours and Company, Wilmington, Del.

[21] Appl. No.: 437,367

[22] Filed: Nov. 1, 1982

Related U.S. Application Data

[63] Continuation-in-part of Ser. No. 337,933, Jan. 7, 1982, abandoned.

[51] Int. Cl.³ .................. C07D 405/12; C07D 409/12; A01N 43/54; A01N 43/66
[52] U.S. Cl. .......................................... 71/92; 71/88; 71/90; 71/91; 71/93; 548/268; 544/209; 544/212; 544/253; 544/278; 544/321; 544/331; 544/332
[58] Field of Search ............... 544/320, 321, 331, 332, 544/278, 253; 71/92, 88, 90, 91

[56] References Cited

U.S. PATENT DOCUMENTS 4,370,480  1/1983  Levitt ................................. 544/320

Primary Examiner—Robert Gerstl

[57] ABSTRACT

This invention relates to ortho-heterocyclicbenzenesulfonylureas and, more particularly, to ortho-furanylbenzenesulfonylureas, ortho-thienylbenzenesulfonylureas or ortho-pyrrolylbenzenesulfonylureas and their use in agriculturally suitable compositions as pre-emergence and/or post-emergence herbicides and as plant growth regulants.

28 Claims, No Drawings

BENZENESULFONAMIDES AS HERBICIDES

Related Application

This application is a continuation-in-part of my copending application U.S. Ser. No. 337,933, filed Jan. 7, 1982, now abandoned.

Background of the Invention

This invention relates to ortho-heterocyclicbenzenesulfonylureas and, more particularly, to orthofuranylbenzenesulfonylureas, ortho-thienylbenzenesulfonylureas or ortho-pyrrolylbenzenesulfonylureas and their use in agriculturally suitable compositions as pre-emergence and/or post-emergence herbicides and as plant growth regulants.

Description of the Prior Art

U.S. Pat. Nos. 4,127,405 and 4,169,719 disclose a broad class of pyrimidine and triazine sulfonylurea compounds.

European Pat. No. 7687 discloses herbicidal sulfonylurea compounds such as, among others,

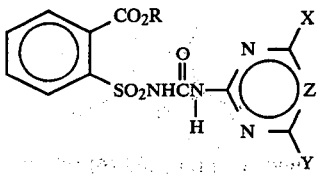

where
X is $CH_3$ or $OCH_3$;
Z is CH or N; and
Y is $C_1-C_4$ alkyl substituted with $OCH_3$, $OC_2H_5$, CN, C(O)L, or 1-3 atoms of F, Cl, or Br, where L is $NH_2$, OH, $N(OCH_3)CH_3$, $NH(C_1-C_4$ alkyl), $N(C_1-C_4$ alkyl) or $C_1-C_6$ alkoxy.

U.S. Ser. No. 264,331 discloses herbicidal o-phenylbenzenesulfonylureas.

Summary of the Invention

This invention relates to compounds of Formula I, suitable agricultural compositions containing them, and their method of use as general and/or selective preemergence and/or postemergence herbicides and as plant growth regulants.

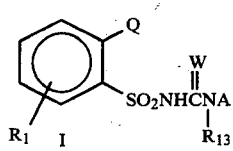

where Q is

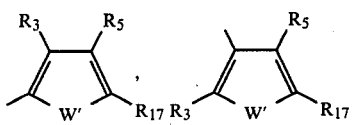

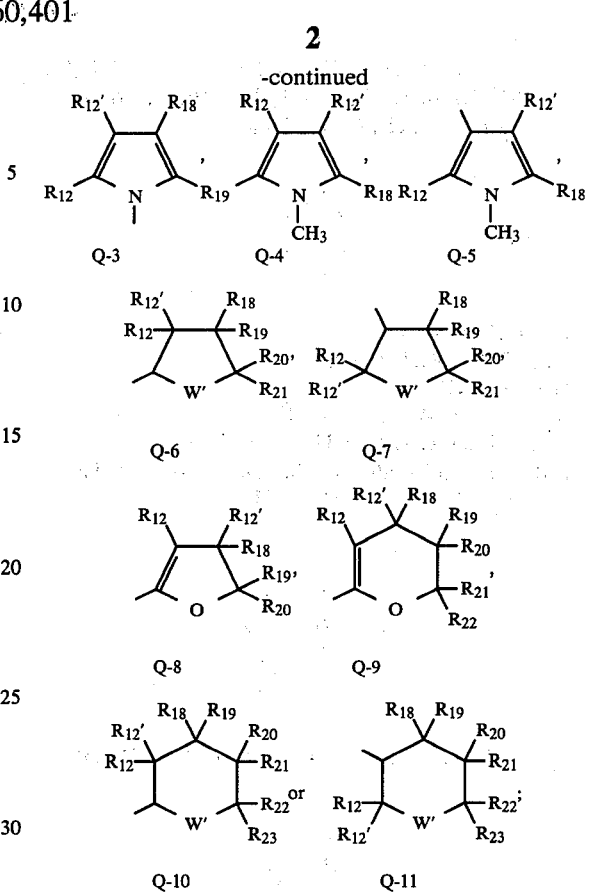

where
W is O or S;
W' is O or S;
$R_1$ is H, F, Cl, Br, $CH_3$, $CF_3$ or $OCH_3$;
$R_3$ is H, $CH_3$, $C_2H_5$, Cl, Br, $OCH_3$ or $OC_2H_5$;
$R_5$ is H, $CH_3$, $C_2H_5$, Cl, Br, $OCH_3$ or $OC_2H_5$;
$R_{17}$ is H, $CH_3$, $C_2H_5$, Cl, Br, $OCH_3$, $OC_2H_5$ or $CO_2CH_3$;
$R_{12}$ is H or $CH_3$;
$R_{12}'$ is H or $CH_3$;
$R_{13}$ is H or $CH_3$;
$R_{18}$ is H or $CH_3$;
$R_{19}$ is H or $CH_3$;
$R_{20}$ is H or $CH_3$;
$R_{21}$ is H or $CH_3$;
$R_{22}$ is H or $CH_3$;
$R_{23}$ is H or $CH_3$;

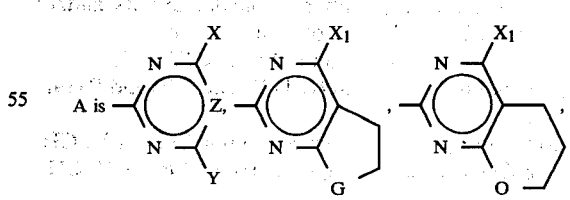

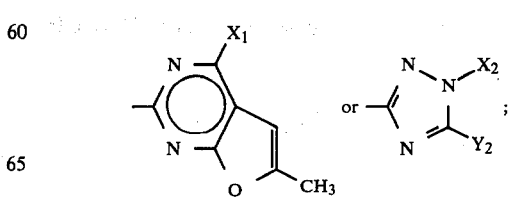

X is $CH_3$, $OCH_3$ or Cl;

Y is CH₃, C₂H₅, CH₂OCH₃, OCH₃, OC₂H₅, CH(OCH₃)₂, SCH₃, CF₃, NH₂, NHCH₃, N(CH₃)₂, OCH₂CH₂OCH₃, OCH₂CF₃ or

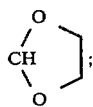;

Z is CH or N;
X₁ is CH₃, OCH₃ or Cl;
G is O or CH₂;
X₂ is C₁-C₃ alkyl or CH₂CF₃;
Y₂ is CH₃O, C₂H₅O, CH₃S or C₂H₅S;
and their agriculturally suitable salts; provided that
(1) when W is S, then R₁₃ is H, A is 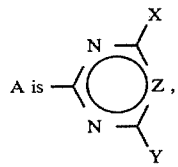, Y is CH₃, OCH₃, C₂H₅, CH₂OCH₃, CH(OCH₃)₂ or

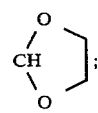;

(2) when Q is

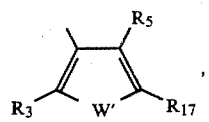, then R₃ is H, CH₃ or C₂H₅; R₅ is H, CH₃ or C₂H₅; and R₁₇ is H, CH₃, C₂H₅ or —CO₂CH₃;
(3) when one of R₃, R₅, R₁₇ is other than H, then the other two substituents are H or CH₃;
(4) the total number of carbon atoms in R₁₂, R₁₂', R₁₈, R₁₉, R₂₀, R₂₁, R₂₂ and R₂₃ is less than or equal to 4;
(5) when X is Cl, then Z is CH and Y is OCH₃, NH₂, OC₂H₅, NHCH₃ or N(CH₃)₂.

Preferred for their higher herbicidal activity and/or their more favorable ease of synthesis are:
(1) Compounds of Formula I where W is O;
(2) Compounds of Preferred (1) where R₁ and R₁₃ are H;
(3) Compounds of Preferred (2) where R₃ is H, CH₃ or C₂H₅; R₅ is H, CH₃ or C₂H₅; and R₁₇ is H, CH₃, C₂H₅ or —CO₂CH₃;
(4) Compounds of Preferred (3) where Y is CH₃, CH₂OCH₃,

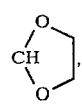, and A is

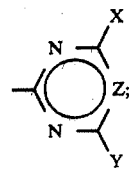;

(5) Compounds of Preferred (4) where Q is

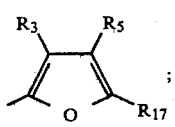;

(6) Compounds of Preferred (4) where Q is

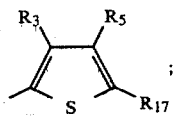;

(7) Compounds of Preferred (4) where Q is

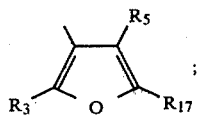;

(8) Compounds of Preferred (4) where Q is

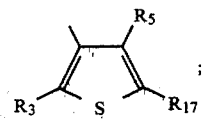;

(9) Compounds of Preferred (4) where Q is

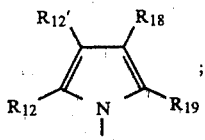;

(10) Compounds of Preferred (4) where Q is

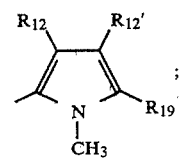;

(11) Compounds of Preferred (4) where Q is

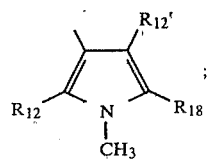;

(12) Compounds of Preferred (4) where Q is $$\begin{array}{c} R_{12}' \quad R_{18} \\ R_{12} \diagup\!\!\!\diagdown\!\!\!\diagup R_{19} \\ \diagdown\!\!\!O\diagup\!\!\!\diagdown R_{20}; \\ R_{21} \end{array}$$

(13) Compounds of Preferred (4) where Q is $$\begin{array}{c} R_{12}' \quad R_{18} \\ R_{12} \diagup\!\!\!\diagdown\!\!\!\diagup R_{19} \\ \diagdown\!\!\!S\diagup\!\!\!\diagdown R_{20}; \\ R_{21} \end{array}$$

(14) Compounds of Preferred (4) where Q is $$\begin{array}{c} R_{18} \\ R_{12}' \diagup\!\!\!\diagdown R_{19} \\ R_{12} \diagup\!\!\!\diagdown O \diagdown R_{20}; \\ R_{21} \end{array}$$

(15) Compounds of Preferred (4) where Q is $$\begin{array}{c} R_{18} \\ R_{12}' \diagup\!\!\!\diagdown R_{19} \\ R_{12} \diagup\!\!\!\diagdown S \diagdown R_{20}; \\ R_{21} \end{array}$$

(16) Compounds of Preferred (4) where Q is $$\begin{array}{c} R_{12} \quad R_{12}' \\ \diagdown\!\!\!=\!\!\!\diagup \\ \diagup\!\!\!\diagdown R_{18} \\ O \diagdown R_{19}; \\ R_{20} \end{array}$$

(17) Compounds of Preferred (4) where Q is $$\begin{array}{c} R_{12}' \quad R_{18} \\ R_{12} \diagdown\!\!\!=\!\!\!\diagup\!\!\!\diagdown R_{19} \\ \diagup\!\!\!\diagdown\!\!\!\diagdown R_{20}; \\ O \quad R_{21} \\ R_{22} \end{array}$$

(18) Compounds of Preferred (4) where Q is $$\begin{array}{c} R_{18} \quad R_{19} \\ R_{12}' \diagup\!\!\!\diagdown\!\!\!\diagup R_{20} \\ R_{12} \diagup\!\!\!\diagdown\!\!\!\diagup R_{21}; \\ \diagdown\!\!\!O\diagup\!\!\!\diagdown R_{22} \\ R_{23} \end{array}$$

(19) Compounds of Preferred (4) where Q $$\begin{array}{c} R_{18} \quad R_{19} \\ R_{12}' \diagup\!\!\!\diagdown\!\!\!\diagup R_{20} \\ R_{12} \diagup\!\!\!\diagdown\!\!\!\diagup R_{21}; \\ \diagdown\!\!\!S\diagup\!\!\!\diagdown R_{22} \\ R_{23} \end{array}$$

(20) Compounds of Preferred (4) where Q $$\begin{array}{c} R_{18} \quad R_{19} \\ \diagup\!\!\!\diagdown\!\!\!\diagup R_{20} \\ R_{12} \diagup\!\!\!\diagdown\!\!\!\diagup R_{21}; \text{ and} \\ R_{12}' \diagdown\!\!\!S\diagup\!\!\!\diagdown R_{22} \\ R_{23} \end{array}$$

(21) Compounds of Preferred (4) where Q $$\begin{array}{c} R_{18} \quad R_{19} \\ \diagup\!\!\!\diagdown\!\!\!\diagup R_{20} \\ R_{12} \diagup\!\!\!\diagdown\!\!\!\diagup R_{21}. \\ R_{12}' \diagdown\!\!\!O\diagup\!\!\!\diagdown R_{22} \\ R_{23} \end{array}$$

Specifically Preferred for reasons of their highest herbicidal activity or most favorable ease of synthesis are:

N-[(4,6-dimethylpyrimidin-2-yl)aminocarbonyl]-2-(tetrahydrofuran-2-yl)benzenesulfonamide;

N-[(4-methoxy-6-methylpyrimidin-2-yl)aminocarbonyl]-2-(tetrahydrofuran-2-yl)benzenesulfonamide;

N-[(4,6-dimethoxypyrimidin-2-yl)aminocarbonyl]-2-(tetrahydrofuran-2-yl)benzenesulfonamide;

N-[(4-chloro-6-methoxypyrimidin-2-yl)aminocarbonyl]-2-(tetrahydrofuran-2-yl)benzenesulfonamide;

N-[(4,6-dimethoxy-1,3,5-triazin-2-yl)aminocarbonyl]-2-(tetrahydrofuran-2-yl)benzenesulfonamide; and N-[(4-methoxy-6-methyl-1,3,5-triazin-2-yl)aminocarbonyl]-2-(tetrahydrofuran-2-yl)benzenesulfonamide.

Detailed Description of the Invention

Synthesis

The ortho-heterocyclicbenzenesulfonylureas of Formula I can be prepared by reacting the appropriately substituted benzenesulfonamide II with an appropriate methyl heteroaryl carbomate III in the presence of an equimolar amount of trimethylaluminum according to the procedure of Equation 1. Unless indicated otherwise, all temperatures are in °C.

Equation 1

$$\underset{R_1}{\underset{II}{\text{[benzene ring with Q and SO}_2\text{NH}_2\text{]}}} + CH_3OC\underset{R_{13}}{\overset{O}{\|}}NA \xrightarrow[CH_2Cl_2]{Al(CH_3)_3} I$$

III wherein $R_1$, $R_{13}$, Q and A are as previously defined, and W is O.

The reaction of Equation 1 is best carried out in methylene chloride at 25° to 40° C. for 24 to 96 hours under a nitrogen atmosphere. The product can be isolated by the addition of an aqueous acetic acid solution followed by extraction of the product into methylene chloride or direct filtration of a product of low solubility. The product can ordinarily be purified by trituration with solvents such as n-butyl chloride or ether or by column chromatography.

Further details of this reaction and the preparation of the carbamates of Formula III can be found in U.S. Ser. No. 337,934.

Compounds of Formula I, in which Q does not include Q-3, Q-4 or Q-5, may also be prepared by reacting the appropriately substituted benzenesulfonyl isocyanate or isothiocyanate with an appropriate aminoheterocycle, V, as shown in Equation 2.

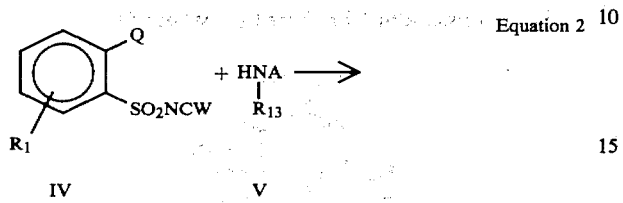

Equation 2

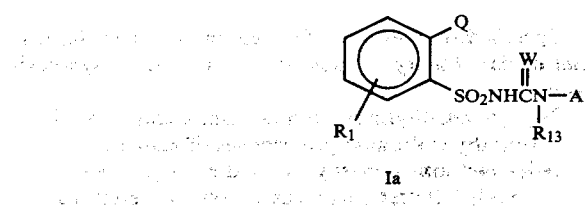

wherein $R_1$, $R_{13}$, W and A are as previously defined, and Q is Q-1, Q-2, and Q-6 to Q-11.

The reaction of Equation 2 can best be carried out in an inert aprotic solvent such as methylene chloride, tetrahydrofuran or acetonitrile at a temperature between 20° and 80°. A catalytic amount of 1,4-diazabicyclo[2,2,2]octane (DABCO) may be used to accelerate the reaction. In cases in which the products are insoluble in the reaction solvent, they may be isolated by simple filtration. When the products are soluble, they may be isolated by evaporation of the solvent and trituration of the residue with solvents such as 1-chlorobutane, ethyl ether or methanol and filtration.

The benzenesulfonyl isocyanates of Formula IVa may be prepared as shown below in Equation 3, by phosgenation of the sulfonamide II in the presence of butyl isocyanate. The sulfonyl isocyanates of Formula IV may also be prepared, as shown in Equation 4, by phosgenation of the butyl ureas of Formula VI.

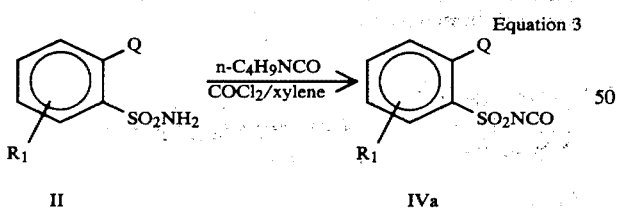

Equation 3 wherein $R_1$ and Q are as defined in Equation 2.

The above reaction can be carried out by heating a mixture of the appropriate sulfonamide (II), an alkyl isocyanate such as butyl isocyanate and a catalytic amount of a tertiary amine such as 1,4-diaza[2,2,2]bicyclooctane (DABCO) in xylene, or other inert solvent of boiling point ≧135° to approximately 135° C. Phosgene can then be added to the mixture over a 1–6 hour period until an excess of phosgene is present as indicated by a drop in the boiling point to less than 130° C. The mixture is then cooled and filtered to remove a small amount of insoluble byproducts. The solvent and the alkyl isocyanate can be distilled off in vacuo leaving a residue of the crude sulfonyl isocyanate, IVa, which can be used without further purification.

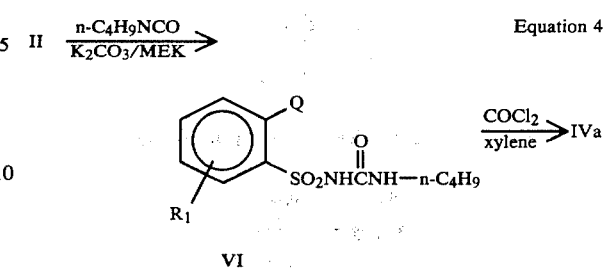

Equation 4 wherein $R_1$ and Q are as defined in Equation 2.

The compounds of Formula VI can be prepared by stirring a mixture of the sulfonamides, II, anhydrous potassium carbonate, and n-butyl isocyanate in acetone or methyl ethyl ketone at 25°–80° until all of the sulfonamide has reacted. The products can be isolated by quenching in dilute mineral acid and recrystallizing the solid product. The compounds VI are then treated with phosgene and a catalytic amount of DABCO in refluxing xylene or chlorobenzene in a manner analogous to that described in Equation 3.

Sulfonylisothiocyanates of Formula IV where W=S can be prepared by treatment of sulfonamides with carbon disulfide and potassium hydroxide followed by the reaction of the dipotassium salt with phosgene according to the teaching of K. Hartke, *Arch. Pharm.*, 299, 174 (1966).

Alternatively, compounds of Formula Ib in which W is S may be prepared by the reaction of the appropriate sulfonamide of Formula II with a heterocyclic isothiocyanate of Formula Va as depicted in Equation 5.

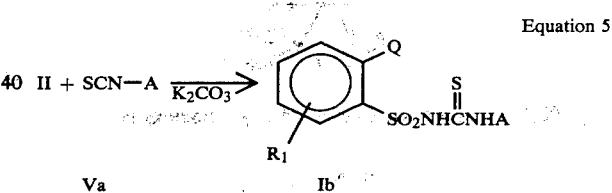

Equation 5 wherein A, Q and $R_1$ are as previously defined.

The reaction of Equation 5 is best carried out by dissolving or suspending the sulfonamide and isothiocyanate in a polar solvent such as acetone, acetonitrile, ethyl acetate or methyl ethyl ketone, adding an equivalent of a base such as potassium carbonate and stirring the mixture at ambient temperature up to the reflux temperature for one to twenty-four hours. In some cases, the product precipitates from the reaction mixture and can be removed by filtration. The product is stirred in dilute mineral acid, filtered and washed with cold water. If the product does not precipitate from the reaction mixture it can be isolated by evaporation of the solvent, trituration of the residue with dilute mineral acid and filtering off the insoluble product.

The heterocyclic isothiocyanates which are used in the procedure of Equation 5 are prepared, for example, according to the method of Japan patent Application Pub: Kokai No. 51-143686, June 5, 1976, or that of W. Abraham and G. Barnikow, *Tetrahedron*, 29, 691-7 (1973).

The synthesis of heterocyclic amine derivatives such as those depicted by Formula V has been reviewed in "The Chemistry of Heterocyclic Compounds", a series published by Interscience Publ., New York and London, and the teachings of which are incorporated herein by reference. Aminopyrimidines are described by D. J. Brown in "The Pyrimidines", Vol. XVI of the above series.

The 5,6-dihydrofuro[2,3-d]pyrimidin-2-amines, the cyclopenta[d]pyrimidin-2-amines, and the 6,7-dihydro-5H-pyrano[2,3-d]pyrimidin-2-amines, are prepared as described in unexamined European patent application No. 15,683. Synthesis of the furo[2,3-d]pyrimidin-2-amines are described in unexamined European patent application No. 46,677. The heterocyclic amines in which A is a triazole ring are disclosed in copending U.S. application Ser. No. 382,711. Pyrimidine and triazine amines in which Y is dimethoxymethyl or 1,3-dioxolan-2-yl are prepared as described in copending U.S. application Ser. No. 328,098.

Sulfonamides of Formula II, in which Q is Q-1 or Q-2, can be prepared by the sequence of reactions shown in Equation 6.

(6a)  Equation 6

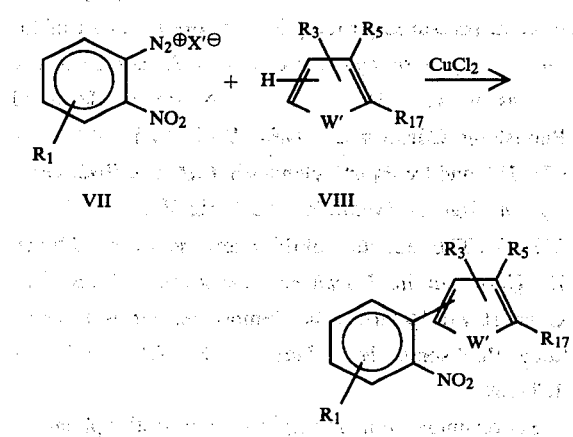

(6b)

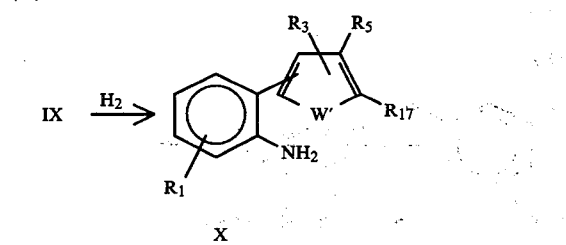

(6c)

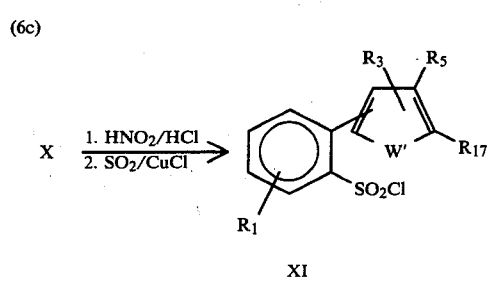

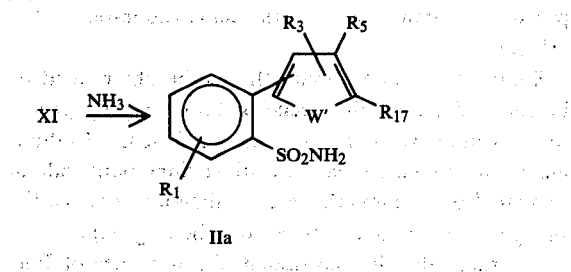

wherein
$R_1$ and W' are as previously defined;
X' is Cl, Br or $HSO_4$;
$R_3$ and $R_5$ and H, $CH_3$ or $C_2H_5$; and
$R_{17}$ is H, $CH_3$, $C_2H_5$ or $CO_2CH_3$.

Reaction (6a):

In this reaction an o-nitrosubstituted phenyl diazonium halide or sulfate is coupled with an appropriately substituted thiophene or furan in the presence of a catalyst such as cupric chloride. The conditions necessary for this transformation are described in Gomberg and Bachmann, *J. Am. Chem. Soc.*, 46, 2339 (1924); J. Johnson, *J. Chem. Soc.*, 895 (1946); and in *J. Pharm. Soc. (Japan)*, 90, 1150-1155 (1970). In cases where both the α- and the β-position of the thiophene or furan are available for coupling, both isomers are usually obtained with the α-coupled product being the predominent isomer. These isomers can be separated by fractional crystallization or chromatography and carried on through the remaining three reactions of Equation 6.

Reaction (6b):

The reduction described in step (6b) is accomplished by treating a solution of the compounds of Formula IX, in a solvent such as ethanol, ethyl acetate, or DMF, in a pressure vessel, with 100-1000 pounds per square inch of hydrogen at 80°-150° in the presence of a hydrogenation catalyst such as 5-10% palladium absorbed on carbon. When the theoretical amount of hydrogen has been absorbed, the solution is then cooled and the catalyst is removed by filtration. The product is then isolated by evaporation of the solvent.

Reaction (6c):

The diazotization and coupling with sulfur dioxide, described in step 6c, is accomplished in the following manner. A solution of the aniline of Formula X in a mixture of concentrated hydrochloric acid and glacial acetic acid is treated with a solution of sodium nitrite in water at −5° to 0° C. After stirring for 10-15 minutes at 0° C. to insure complete diazotization, this solution is added to a mixture of an excess of sulfur dioxide, and a catalytic amount of cuprous chloride in glacial acetic acid at 0°-5°. The temperature is kept at 0°-5° for ¼ to 1 hour then raised to 20°-25° and held at that temperature for 2-4 hours. This solution is then poured into a large excess of ice water, and the sulfonyl chloride products, XI, is isolated by filtration or by extraction into a solvent such as ethyl ether or methylene chloride followed by evaporation of the solvent.

Reaction (6d):

The amination described in step (6d) is carried out by treating a solution of the sulfonyl chloride of Formula XI with an excess of anhydrous ammonia in a solvent such as ethyl ether or methylene chloride at 0°-25° C. If the product sulfonamide, II, is insoluble, it may be isolated by filtration followed by washing out the salts with water. If the product sulfonamide is soluble in the reaction solution, it may be isolated by filtering off the precipitated ammonium chloride and evaporation of the solvent.

Sulfonamides of Formula IIa can be chlorinated or brominated on the thiophene or furan ring by procedures well known in the art. These halogenated sulfonamides may then be reacted with sodium methoxide in methanol or sodium ethoxide in ethanol to replace the halogen atom with a methoxy or ethoxy group.

Alternatively, the substituted nitrobenzenes of Formula IX can be prepared by the procedure shown in Equation 7.

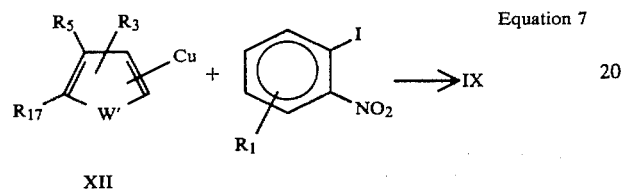

wherein $R_1$, $R_3$, $R_5$, $R_{17}$, and $W'$ are as previously defined.

In the reaction shown in Equation 7, a furyl- or thienyl copper compound of Formula XII is reacted with an iodonitrobenzene in a solvent such as pyridine or quinoline. The copper compounds of Formula XII are prepared by reacting the corresponding lithium compounds with cuprous iodide or cuprous bromide in a solvent such as diethyl ether. The detailed procedures for these types of reactions are described in the following references: M. Nilsson and C. Ullenius, *Acta. Chem. Scand.*, 24, 2379–2388 (1970); C. Ullenius, *Acta. Chem. Scand.*, 26, 3383–3386 (1972).

Sulfonamides containing a tetrahydrofuran or tetrahydrothiophene group (Formula II, Q=Q-6 and Q-7) can be prepared by catalytic reduction of the corresponding furan or thiophene compounds as shown in Equation 8.

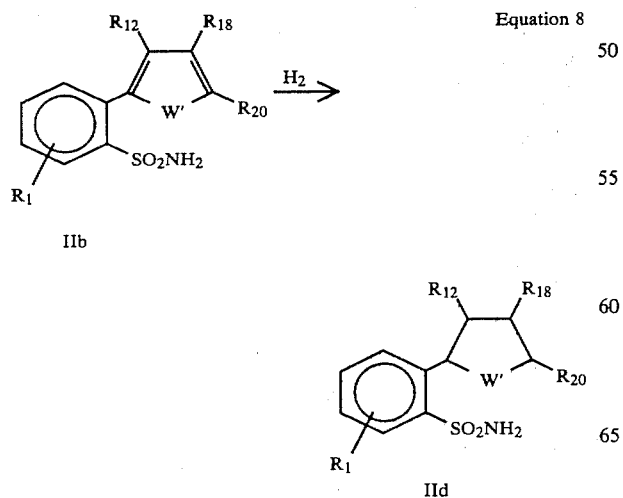

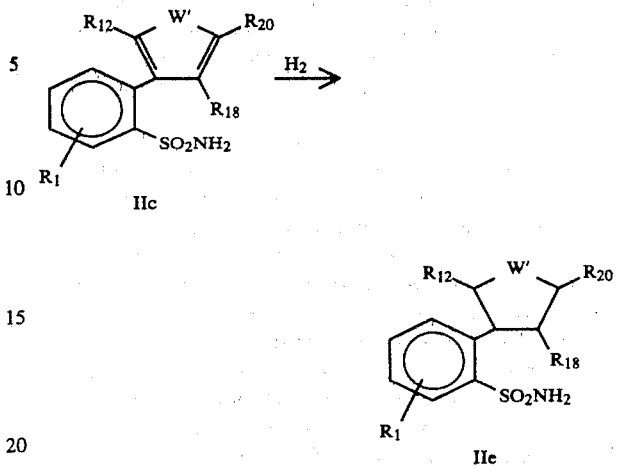

wherein $R_1$, $R_{12}$, $R_{18}$, $R_{20}$, and $W'$ are as previously defined.

Selective reductions of the type shown in Equation 8 are well known in the literature. The choice of catalyst, solvent, pressure and temperature for reduction of furans has been reviewed by Samuel Sevadesh in *The Furans* by A. P. Dunlop and F. N. Peters, Reinhold Publishing Corporation, New York, N.Y. 1953, pp. 674–713; and by P. N. Rylander in *Catalytic Hydrogenation in Organic Synthesis*, Academic Press, 1979, pp. 227–234. The reduction of thiophenes is reviewed by H. D. Hartough in *Thiophene and Its Derivatives*, The Chemistry of Heterocyclic Compounds Series, Interscience Publishers, Inc., New York, N.Y. 1952, pp. 167–169.

Sulfonamides containing a tetrahydrothiophene or tetrahydrothiopyran group can also be prepared by the sequence of reactions shown in Equation 9.

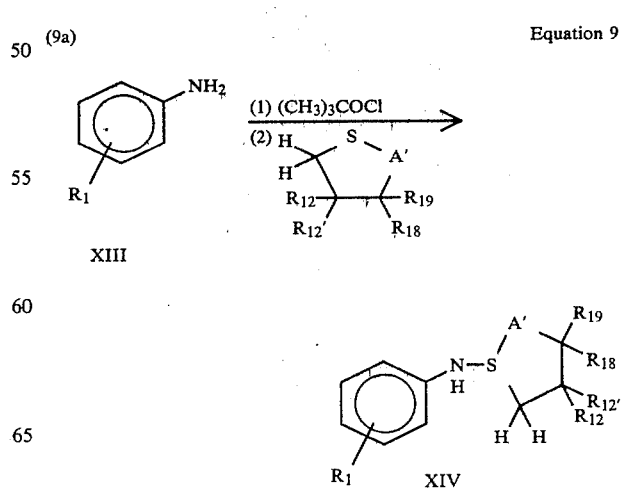

-continued (9b)

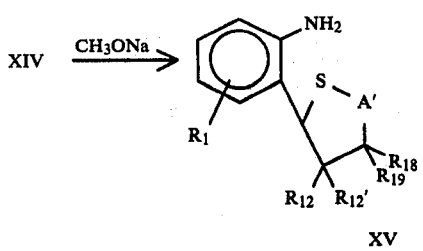

(9c)

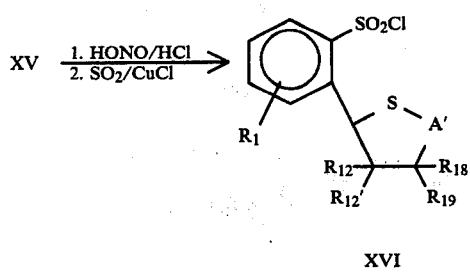

(9d)

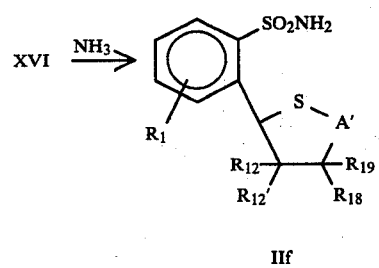

wherein

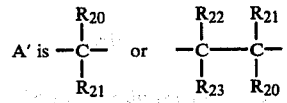

$R_1$, $R_{12}$, $R_{12'}$, $R_{18}$, $R_{19}$, $R_{20}$, $R_{21}$, $R_{22}$ and $R_{23}$ are as previously defined.

The general conditions used to carry out the reactions described in Reactions (9a) and (9b) are described by P. G. Gassman and G. D. Gruetzmacher, *J. Am. Chem. Soc.*, 96, 5487–5495 (1974). The procedures shown in Reactions (9c) and (9d) are directly analogous to those described in Reactions (6c) and (6d).

Other sulfonamides containing tetrahydrofuran or tetrahydropyran groups can be prepared by the sequence of reactions shown in Equation 10.

(10a)   Equation 10

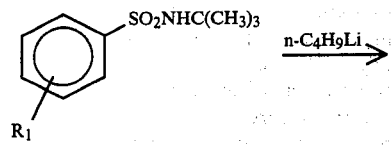

-continued

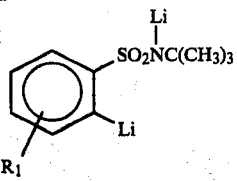

(10b)

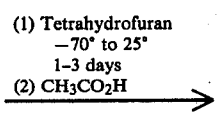

(1) Tetrahydrofuran
 −70° to 25°
 1–3 days
(2) $CH_3CO_2H$

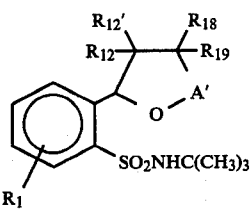

(10c)

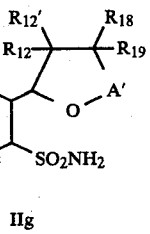

wherein
 A', $R_1$, $R_{12}$, $R_{12'}$, $R_{18}$, $R_{19}$, $R_{20}$, $R_{21}$, $R_{22}$ and $R_{23}$ are as previously defined; and
 X" is Cl or Br.

Reaction (10a):

In this reaction a tert-butyl sulfonamide of Formula XVII is treated with two equivalents of n-butyl lithium at −50° to −80° in tetrahydrofuran solution to give the dilithio salt XVIII.

Reaction (10b):

The salt XVIII is then immediately treated with one equivalent of a chloro- or bromoaldehyde of Formula XXI at −70° to −80°. The temperature is raised to 25° for 1 to 3 days, and the reaction is then quenched by the addition of an acid such as acetic acid. The pure product, XIX, is isolated by stripping off the solvent and chromatographing or recrystallizing the crude product.

Reaction (10c):

In this step the tert-butyl group is removed from XIX by heating these compounds in trifluoroacetic acid at 72° for 1–6 hours. The sulfonamides of Formula IIg are isolated in pure form by stripping off the trifluoroacetic acid solvent.

Sulfonamides of Formula IIj, which contain a dihydrofuran or a dihydropyran group, can be prepared by the method shown in Equation 11.

Equation 11

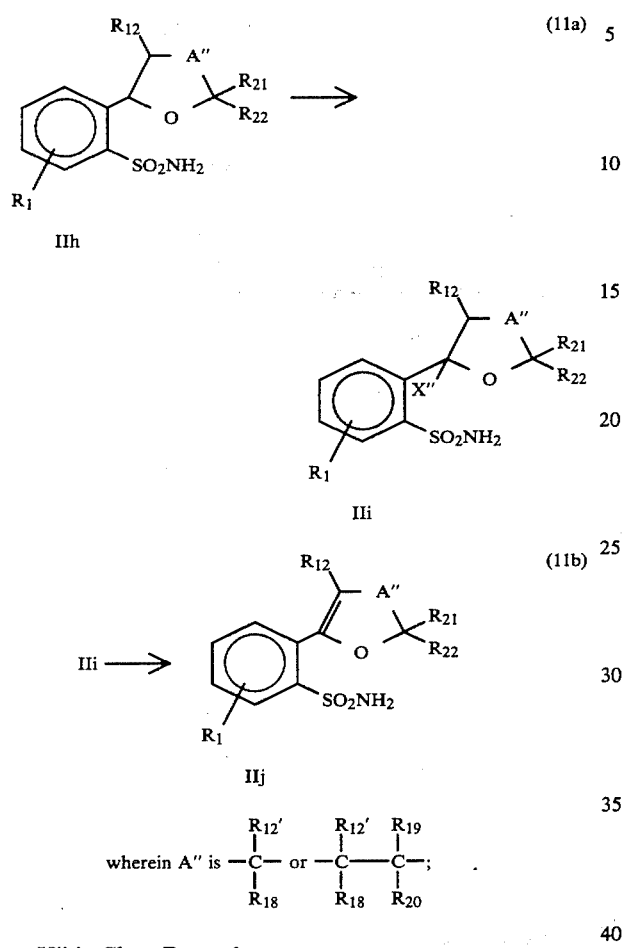

wherein A" is $-\underset{R_{18}}{\overset{R_{12'}}{\underset{|}{\overset{|}{C}}}}-$ or $-\underset{R_{18}}{\overset{R_{12'}}{\underset{|}{\overset{|}{C}}}}-\underset{R_{20}}{\overset{R_{19}}{\underset{|}{\overset{|}{C}}}}-$;

X" is Cl or Br; and $R_1$, $R_{12}$, $R_{12'}$, $R_{18}$, $R_{19}$, $R_{20}$, $R_{21}$, and $R_{22}$ are as previously defined.

Reaction (11a):

In this reaction a sulfonamide of Formula IIh is treated with one equivalent of N-chlorosuccinimide or N-bromosuccinimide at 0°-60° in a solvent such as carbon tetrachloride or chloroform for 2-24 hours. The by-product succinimide is removed by filtration and the solution carried directly on to the next step.

Reaction (11b):

The sulfonamides of Formula IIi are dehydrohalogenated in carbon tetrachloride or chloroform solution by treatment with at least one equivalent of an appropriate base such as triethylamine, DABCO, pyridine, sodium methoxide or anhydrous potassium carbonate at 0°-60° for 1-6 hours. The products are isolated by washing the organic solution with water, drying, and stripping off the solvent. The sulfonamides of Formula IIj can be obtained in pure form by recrystallization from a solvent such as ethanol, 1-chlorobutane, or acetonitrile, or by column chromatography.

Sulfonamides containing a pyrrole group can be prepared by the sequence of reactions shown in Equation 12.

Equation 12

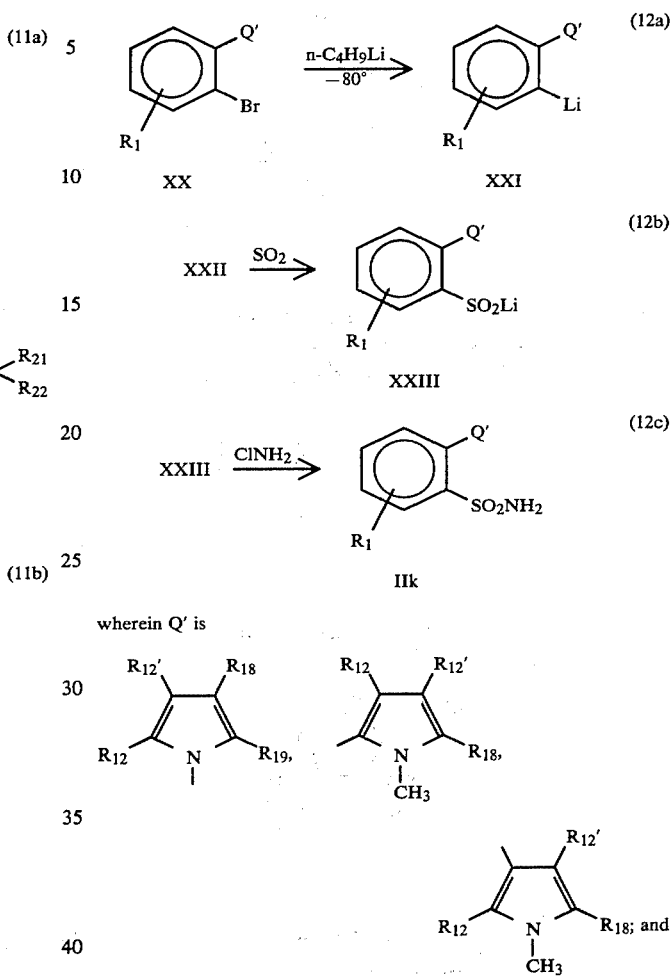

wherein Q' is $R_1$, $R_{12}$, $R_{12'}$, $R_{18}$, and $R_{19}$ are as previously defined.

Reaction (12a):

The lithio compounds of Formula XXI are prepared from the bromo compounds of Formula XX by treatment with n-butyl lithium at $-80°$ in either hexane/ether or hexane/tetrahydrofuran solvent systems. The details of this type of transmetallation are further described by M. E. K. Cartoon and G. W. H. Cheeseman in *J. Organometallic Chemistry*, 212, 1-9 (1981).

Reaction (12b):

The lithio compounds, XXII, are immediately treated with at least one equivalent of sulfur dioxide at 0° to $-50°$. After warming to 25°, the lithium sulfinates of Formula XXIII are filtered off, and can be carried directly on to reaction (12c).

Reaction (12c):

In this step chloramine is prepared at 0° by the addition of aqueous sodium hypochlorite to a stirred mixture of 30% ammonium hydroxide solution and diethyl ether. The lithium sulfinates of Formula XXIII are added to this mixture at 0° and the resulting mixture stirred at room temperature for 2-24 hours. The product sulfonamides are isolated by extraction into a solvent such as ethyl acetate and evaporation of the solvent. The sulfonamides of Formula IIk may be purified by recrystallization from solvents such as ethanol, 1- chlorobutane, or acetonitrile, or by column chromatography.

The bromo compounds of Formula XX can be prepared by methods well known in the art, such as those reviewed by A. R. Jones and G. P. Bean in *The Chemistry of Pyrroles*, Academic Press, New York, N.Y., 1977.

Sulfonamides of Formula II in which Q is Q-11 can be prepared by the sequence of reactions shown in Equation 13.

Reaction (13a):

The dilithio salt of Formula XVIII is prepared as described above in reaction (10a) then treated with a ketone of Formula XXIV at $-70°$ to $-80°$. The temperature is raised to 25° for 1 to 3 days, and the reaction is then quenched by the addition of an acid such as acetic acid. The product, XXV, is isolated by evaporation of the solvent followed by chromatography or recrystallization.

Equation 13

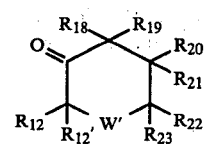

XVIII

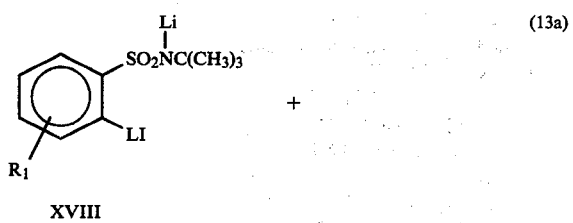

XXIV

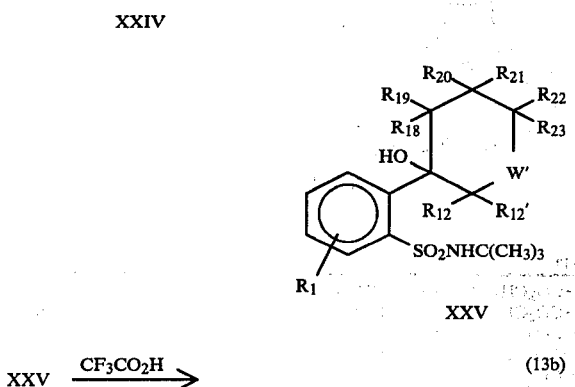

XXV

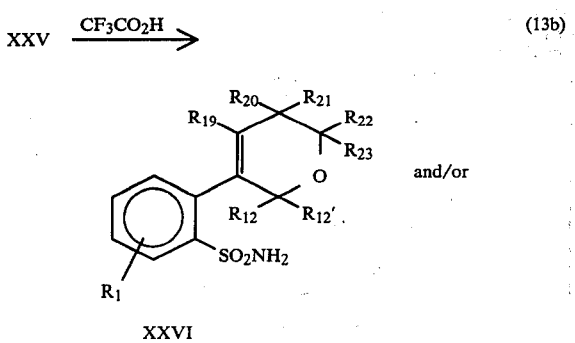

XXVI

-continued
Equation 13

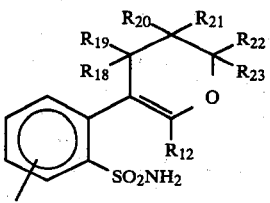

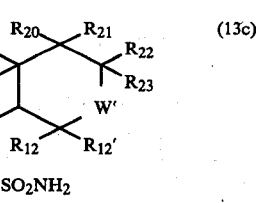

XXVII wherein $R_1$, $R_{12}$, $R_{12}'$, $R_{18}$, $R_{19}$, $R_{20}$, $R_{21}$, $R_{22}$, $R_{23}$ and W' are as previously defined and at least one of $R_{12}$, $R_{12}'$, $R_{18}$ or $R_{19}$ is hydrogen.

Reaction (13b):

Removal of the tert-butyl group is accomplished by heating the above products, XXV, in trifluoroacetic acid at 72° for 1-6 hours. Dehydration of the tertiary hydroxyl group occurs simultaneously and the isomeric mixture of olefinic sulfonamides, XXVI, are isolated upon evaporation of the trifluoroacetic acid solvent.

In reaction (13c), sulfonamides of Formula XXVII are produced upon hydrogenation of the olefins, XXVI, under standard conditions.

Agriculturally suitable salts of compounds of Formula I are also useful herbicides and can be prepared in a number of ways known to the art. For example, metal salts can be made by treating compounds of Formula I with a solution of an alkali or alkaline earth metal salt having a sufficiently basic anion (e.g., hydroxide, alkoxide, carbonate or hydride). Quaternary amine salts can be made by similar techniques. Detailed examples of such techniques are given in U.S. Pat. No. 4,127,405, the disclosure of which is herein incorporated by reference.

The compounds of this invention and their preparation are further illustrated by the following examples wherein temperatures are given in degrees centigrade and all parts are by weight unless otherwise indicated.

Example 1

Methyl 5-[(2-aminosulfonyl)phenyl]furan-2-carboxylate

To a solution of 65.1 g of methyl 5-(2-aminophenyl)-furan-2-carboxylate in a mixture of 270 ml of concentrated hydrochloric acid and 75 ml of glacial acetic acid was added a solution of 25.8 g of sodium nitrite in 75 ml of water at $-5°$ to 0° dropwise over a 30-minute period. The resulting solution was stirred an additional 10 minutes at 0° before being slowly added to a mixture of 6.0 g of cuprous chloride and 50 ml of sulfur dioxide in 375 ml of glacial acetic acid at $\sim 5°$. This reaction mass was stirred at 0° for 1 hour and at 25° for 2 hours before being poured into 2.2 l of ice water. The intermediate sulfonyl chloride precipitated as an oil and was extracted into 1-chlorobutane, washed with water, 5% sodium bicarbonate solution, and dried over anhydrous magnesium sulfate.

The solution of the sulfonyl chloride in 1-chlorobutane was cooled to 5° and treated with 13.5 ml of anhydrous ammonia at 5°-10°. After stirring for 30 minutes at 25°, the reaction mass was filtered and the solid washed well with water and then 1-chlorobutane. The solid was dried in vacuo at 60° to give 20.9 g of the title compound, mp=186.5-188.5°.

NMR (DMSO-$d_6$) δ: 3.8 (s, 2.7 H, $CO_2CH_3$); 7.1-8.3 (m, 8.3 H, 6 aromatics+$SO_2NH_2$).

Example 2

2-(2-Carbomethoxyfur-5-yl)-N-(butylaminocarbonyl)-benzenesulfonamide

A mixture of 16.9 g of the product of Example 1, 7.5 g of n-butyl isocyanate, and 10.4 g of anhydrous potassium carbonate in 150 ml of 2-butanone was stirred at 80° for 3 hours. The reaction mixture was cooled to 25°, poured into 550 ml of ice water and acidified to pH=1 with concentrated hydrochloric acid. The precipitated solid was filtered, washed with water, and dried at 60° in vacuo to give 22.5 g of the title compound, mp=145°-148°.

NMR (DMSO-$d_6$)δ: 0.7-1.5 (m, 7.5 H, 7 butyl's);
2.8-3.1 (m, 3.0 H, 2 butyl's);
3.9 (s, 2.8 H, $CO_2CH_3$);
6.2-6.5 (t, 0.9 H, NH);
7.0-7.5 (m, 1.9 H, 2 furan's);
7.6-8.5 (m, 4.2 H, 4 aromatics);
~10.3 (broad singlet, 0.7 H, NH).

Example 3

2-(2-Carbomethoxyfur-5-yl)benzenesulfonyl isocyanate

A solution of 19.0 g of the product of Example 2 and 0.1 g of 1,4-diazabicyclo[2.2.2.]octane (DABCO) in 90 ml of dry xylenes was heated to reflux temperature (139°). To this solution was added 3.6 ml of liquid phosgene over a period of about 2 hours, keeping the temperature between 125° and 136° by adjusting the rate of phosgene addition. The reaction mixture was cooled to 25°, and filtered under nitrogen to remove DABCO hydrochloride. The filtrate was concentrated in vacuo to give the title compound as a viscous, moisture-sensitive oil. This material was carried on to the desired products without further purification.

IR (neat)=2280 cm$^{-1}$ ($SO_2NCO$);
1760 cm$^{-1}$ (—$CO_2CH_3$).

Example 4

2-(2-Carbomethoxyfur-5-yl)-N-[(4,6-dimethoxypyrimidin-2yl)aminocarbonyl]benzenesulfonamide Under a nitrogen atmosphere, a mixture of 2.5 g of the product of Example 3, 0.9 g of 2-amino-4,6-dimethoxypyrimidine, and a few crystals of DABCO in 15 ml of dry acetonitrile was heated at 50°-55° for 1 hour, then stirred at 25° overnight. The solid was filtered off, washed with acetonitrile and 1-chlorobutane, and dried at 60° in vacuo to give 2.5 g of the title compound, mp=215°-217°(d).

NMR (DMSO-$d_6$) δ: 3.6, 3.8 (two singlets, 8.4 H, 3 $CH_3O$'s);
5.9 (s, 1.2 H, Het-H);
6.9-8.4 (m, 6.2 H, 6 aromatics);
10.7 (s, 1.0 H, NH);
12-13 (broad, 1.1 H, NH).
Anal. Calcd. for $C_{19}H_{18}N_4O_8S$:
C, 49.4; H, 3.9; N, 12.1.
Found:
$C_1$49.6; H, 4.0; N, 12.4;
$C_1$49.8; H, 4.1; N, 12.7.

Using the procedures described in the Equations and Examples above, the compounds described in Tables 1-15 can be prepared.

TABLE 1

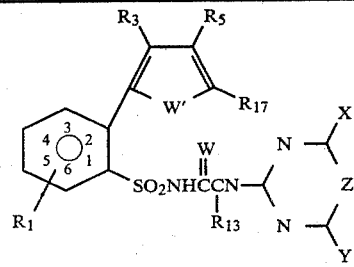

| R1 | W | R3 | R5 | R13 | R17 | W' | Z | X | Y | m.p. (°C.) |
|---|---|---|---|---|---|---|---|---|---|---|
| H | O | H | H | H | —$CO_2CH_3$ | O | CH | $CH_3O$ | $CH_3O$ | 215-217(d) |
| H | O | H | H | H | —$CO_2CH_3$ | O | N | $CH_3O$ | $CH_3O$ | 210-212(d) |
| H | O | H | H | H | —$CO_2CH_3$ | O | CH | $CH_3O$ | $CH_3$ | 200-202(d) |
| H | O | H | H | H | —$CO_2CH_3$ | O | N | $CH_3O$ | $CH_3$ | 198-199(d) |
| H | O | H | H | H | —$CO_2CH_3$ | O | CH | $CH_3$ | $CH_3$ | 197-199(d) |
| H | O | H | H | H | —$CO_2CH_3$ | O | N | $CH_3$ | $CH_3$ | 205-207(d) |
| H | O | H | H | H | H | O | CH | $CH_3O$ | $CH_3O$ | 168-183(d) |
| H | O | H | H | H | H | O | N | $CH_3O$ | $CH_3O$ | 175(d) |
| H | O | H | H | H | H | O | CH | $CH_3O$ | $CH_3$ | 162-168(d) |
| H | S | H | H | H | H | O | N | $CH_3O$ | $CH_3$ | |
| H | S | H | H | H | H | O | CH | $CH_3$ | $CH_3$ | |
| H | O | H | H | H | H | O | N | $CH_3$ | $CH_3$ | |
| H | O | H | H | $CH_3$ | H | O | N | $CH_3O$ | $CH_3O$ | |
| H | O | H | H | H | H | S | CH | $CH_3O$ | $CH_3O$ | 193-196°d |
| H | O | H | H | H | H | S | CH | $CH_3O$ | $CH_3$ | 218-219°d |
| H | O | H | H | H | H | S | CH | $CH_3$ | $CH_3$ | 211-215° |
| H | O | H | H | H | H | S | N | $CH_3O$ | $CH_3O$ | >260° |
| H | O | H | H | H | H | S | N | $CH_3O$ | $CH_3$ | 190-196°d |
| H | O | H | H | H | H | S | N | $CH_3$ | $CH_3$ | |
| H | O | H | H | H | H | O | N | $CH_3O$ | $CH_3$ | 165-186(d) |

TABLE 1-continued

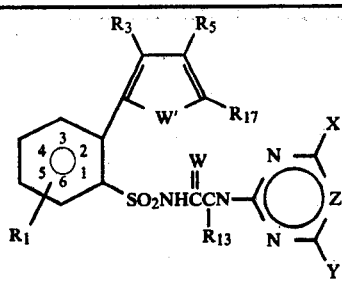

| R1 | W | R3 | R5 | R13 | R17 | W' | Z | X | Y | m.p. (°C.) |
|---|---|---|---|---|---|---|---|---|---|---|
| 5-F | O | H | H | H | H | O | N | CH3O | CH3 | |
| 5-Cl | O | H | H | H | H | O | N | CH3O | CH3 | |
| 5-Br | O | H | H | H | H | O | N | CH3O | CH3 | |
| 5-CF3 | O | H | H | H | H | O | N | CH3O | CH3 | |
| H | O | H | H | H | H | O | CH | CH3 | CH3 | 162–178(d) |
| 5-CH3 | O | H | H | H | H | O | N | CH3O | CH3 | |
| 5-CH3O | O | H | H | H | H | O | N | CH3O | CH3 | |
| 3-Cl | O | H | H | H | H | O | N | CH3O | CH3 | |
| 4-Cl | O | H | H | H | H | O | N | CH3O | CH3 | |
| 6-Cl | O | H | H | H | H | O | N | CH3O | CH3 | |
| H | O | CH3 | H | H | H | O | N | CH3O | CH3 | |
| H | O | C2H5 | H | H | H | O | N | CH3O | CH3 | |
| H | O | Cl | H | H | H | O | N | CH3O | CH3 | |
| H | O | Br | H | H | H | O | N | CH3O | CH3 | |
| H | O | CH3O | H | H | H | O | N | CH3O | CH3 | |
| H | O | C2H5O | H | H | H | O | N | CH3O | CH3 | |
| H | O | H | CH3 | H | H | O | N | CH3O | CH3 | |
| H | O | H | Cl | H | H | O | N | CH3O | CH3 | |
| H | O | H | CH3O | H | H | O | N | CH3O | CH3 | |
| H | O | CH3 | CH3 | H | CH3 | O | N | CH3O | CH3 | |
| H | S | H | H | H | CH3 | O | N | CH3O | CH3 | |
| H | O | H | H | H | C2H5 | O | N | CH3O | CH3 | |
| H | O | H | H | H | Cl | O | N | CH3O | CH3 | |
| H | O | H | H | H | Br | O | N | CH3O | CH3 | |
| H | O | H | H | H | CH3O | O | N | CH3O | CH3 | |
| H | O | H | H | H | C2H5O | O | N | CH3O | CH3 | |
| H | O | H | H | H | H | O | N | CH3O | CH3 | |
| H | O | H | H | H | H | O | CH | Cl | CH3O | |
| H | O | H | H | H | H | O | CH | Cl | NH2 | |
| H | O | H | H | H | H | O | CH | CH3 | —CH2OCH3 | |
| H | O | H | H | H | H | O | CH | CH3 | C2H5O | |
| H | O | H | H | H | H | O | CH | CH3 | CH(OCH3)2 | |
| H | O | H | H | H | H | O | CH | CH3O | C2H5— | |
| H | O | H | H | H | H | O | N | CH3O | NH2 | |
| H | O | H | H | H | H | O | N | CH3O | NHCH3 | |
| H | O | H | H | H | H | O | N | CH3O | N(CH3)2 | |
| H | O | H | H | H | H | O | CH | CH3 | CH(—OCH2CH2O—) | |
| H | O | H | H | H | H | O | CH | CH3 | OCH2CF3 | |
| H | O | H | H | H | H | O | CH | OCH3 | CF3 | |
| H | O | H | H | H | H | O | CH | CH3 | OCH2CH2OCH3 | |
| H | O | H | H | H | H | O | N | CH3 | SCH3 | |

TABLE 2

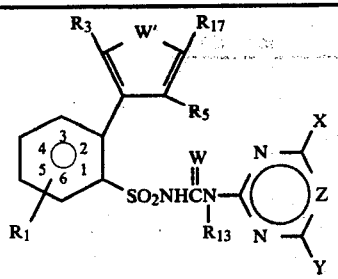

| R1 | W | R3 | R5 | R13 | R17 | W' | Z | X | Y | m.p. (°C.) |
|---|---|---|---|---|---|---|---|---|---|---|
| H | O | H | H | H | H | O | CH | CH3O | CH3O | |
| H | O | H | H | H | H | O | CH | CH3O | CH3 | |
| H | O | H | H | H | H | O | CH | CH3 | CH3 | |
| H | O | H | H | H | H | O | N | CH3O | CH3O | |
| H | O | H | H | H | H | O | N | CH3O | CH3 | |
| H | O | H | H | H | H | O | N | CH3 | CH3 | |
| H | O | H | H | H | H | S | N | CH3O | CH3 | |

TABLE 2-continued

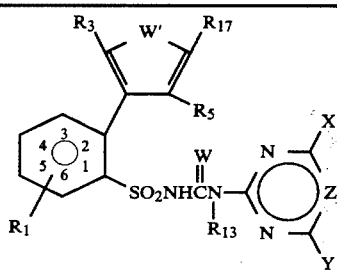

| R₁ | W | R₃ | R₅ | R₁₃ | R₁₇ | W' | Z | X | Y | m.p. (°C.) |
|---|---|---|---|---|---|---|---|---|---|---|
| H | O | H | H | H | H | S | N | CH₃O | CH₃O | |
| H | O | H | H | H | H | S | CH | CH₃O | CH₃O | |
| H | S | H | H | H | H | S | CH | CH₃O | CH₃ | |
| H | O | H | H | H | H | S | CH | CH₃ | CH₃ | |
| H | O | H | H | CH₃ | H | O | N | CH₃O | CH₃O | |
| 5-Cl | O | H | H | H | H | O | N | CH₃O | CH₃O | |
| 5-Br | O | H | H | H | H | O | N | CH₃O | CH₃ | |
| 5-CH₃ | O | H | H | H | H | O | N | CH₃O | CH₃ | |
| 6-Cl | O | H | H | H | H | O | N | CH₃O | CH₃ | |
| 6-CH₃ | O | H | H | H | H | O | N | CH₃O | CH₃ | |
| H | O | CH₃ | H | H | H | O | N | CH₃O | CH₃ | |
| H | O | C₂H₅ | H | H | H | O | N | CH₃O | CH₃ | |
| H | O | CH₃ | CH₃ | H | CH₃ | O | N | CH₃O | CH₃ | |
| H | O | H | CH₃ | H | H | O | N | CH₃O | CH₃ | |
| H | S | H | H | H | C₂H₅ | O | N | CH₃O | CH₃ | |
| H | O | H | H | H | CO₂CH₃ | O | N | CH₃O | CH₃ | |
| H | O | H | H | H | H | O | N | CH₃O | CH₃O | |
| H | O | H | H | H | H | O | CH | CH₃O | CH₃O | |
| H | O | H | H | H | H | O | CH | CH₃O | CH₃ | |
| H | O | H | H | H | H | O | CH | Cl | CH₃O | |
| H | O | H | H | H | H | O | CH | CH₃ | CH₂OCH₃ | |
| H | S | H | H | H | H | O | CH | CH₃ | CH(OCH₃)₂ | |
| H | O | H | H | H | H | O | N | CH₃O | NH₂ | |
| H | O | H | H | H | H | O | N | CH₃O | NHCH₃ | |
| H | O | H | H | H | H | O | N | CH₃O | N(CH₃)₂ | |
| H | O | H | H | H | H | O | CH | CH₃ | OCH₂CF₃ | |
| H | O | H | H | H | H | O | CH | OCH₃ | CH(—OCH₂CH₂O—) | |

TABLE 3

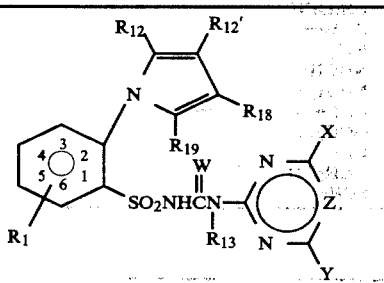

| R₁ | W | R₁₂ | R₁₂' | R₁₃ | R₁₈ | R₁₉ | Z | X | Y | m.p. (°C.) |
|---|---|---|---|---|---|---|---|---|---|---|
| H | O | H | H | H | H | H | CH | CH₃O | CH₃O | |
| H | O | H | H | H | H | H | CH | CH₃O | CH₃ | |
| H | O | H | H | H | H | H | CH | CH₃ | CH₃ | |
| H | S | H | H | H | H | H | N | CH₃O | CH₃O | |
| H | O | H | H | H | H | H | N | CH₃O | CH₃ | |
| H | O | H | H | H | H | H | N | CH₃ | CH₃ | |
| H | O | CH₃ | H | H | H | CH₃ | CH | CH₃O | CH₃O | |
| H | O | CH₃ | H | H | H | CH₃ | CH | CH₃O | CH₃ | |
| H | O | CH₃ | H | H | H | CH₃ | CH | CH₃ | CH₃ | |
| H | O | CH₃ | H | H | H | CH₃ | N | CH₃O | CH₃O | |
| H | O | CH₃ | H | H | H | CH₃ | N | CH₃O | CH₃ | |
| H | O | H | H | CH₃ | H | H | N | CH₃O | CH₃O | |
| 5-Cl | O | H | H | H | H | H | N | CH₃O | CH₃O | |
| 5-F | O | H | H | H | H | H | N | CH₃O | CH₃ | |
| 5-Br | O | H | H | H | H | H | N | CH₃O | CH₃ | |
| 5-CH₃ | O | H | H | H | H | H | N | CH₃O | CH₃ | |
| 5-CF₃ | O | H | H | H | H | H | N | CH₃O | CH₃ | |
| 5-OCH₃ | O | H | H | H | H | H | N | CH₃O | CH₃ | |
| 3-Cl | O | H | H | H | H | H | N | CH₃O | CH₃ | |
| 4-Cl | O | H | H | H | H | H | N | CH₃O | CH₃ | |

TABLE 3-continued

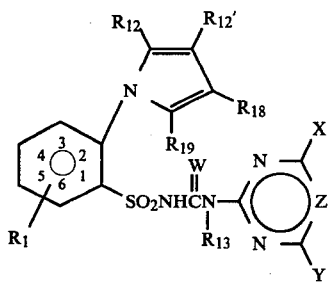

| R1 | W | R12 | R12' | R13 | R18 | R19 | Z | X | Y | m.p. (°C.) |
|---|---|---|---|---|---|---|---|---|---|---|
| 6-Cl | O | H | H | H | H | H | N | CH3O | CH3 | |
| H | O | CH3 | CH3 | H | CH3 | CH3 | N | CH3O | CH3 | |
| H | O | CH3 | H | H | H | H | N | CH3O | CH3 | |
| H | O | H | CH3 | H | H | H | N | CH3O | CH3 | |
| H | O | H | CH3 | H | CH3 | H | N | CH3O | CH3 | |
| H | O | CH3 | CH3 | H | H | H | N | CH3O | CH3 | |
| H | O | H | H | H | H | H | CH | CH3 | C2H5O | |
| H | S | H | H | H | H | H | CH | CH3 | CH2OCH3 | |
| H | O | H | H | H | H | H | CH | CH3 | CH(OCH3)2 | |
| H | O | H | H | H | H | H | CH | Cl | CH3O | |
| H | O | H | H | H | H | H | N | CH3O | N(CH3)2 | |
| H | O | H | H | H | H | H | N | CH3O | NH2 | |

TABLE 4

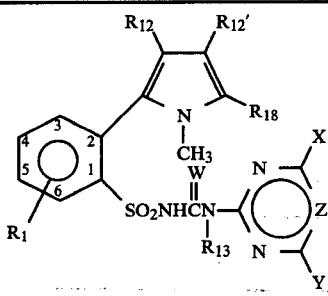

| R1 | W | R12 | R12' | R13 | R18 | Z | X | Y | m.p. (°C.) |
|---|---|---|---|---|---|---|---|---|---|
| H | O | H | H | H | H | CH | CH3O | CH3O | |
| H | O | H | H | H | H | CH | CH3O | CH3 | |
| H | O | H | H | H | H | CH | CH3 | CH3 | |
| H | O | H | H | H | H | N | CH3O | CH3O | |
| H | O | H | H | H | H | N | CH3O | CH3 | |
| H | O | H | H | H | CH3 | CH | CH3O | CH3O | |
| H | O | H | H | H | CH3 | CH | CH3O | CH3 | |
| H | S | H | H | H | CH3 | N | CH3O | CH3O | |
| H | O | H | H | H | CH3 | N | CH3O | CH3 | |
| H | O | CH3 | CH3 | H | CH3 | N | CH3O | CH3 | |
| H | O | CH3 | CH3 | H | H | N | CH3O | CH3 | |
| H | S | CH3 | H | H | H | N | CH3O | CH3 | |
| H | O | H | CH3 | H | H | N | CH3O | CH3 | |
| H | O | H | H | CH3 | H | N | CH3O | CH3O | |
| 5-F | O | H | H | H | H | N | CH3O | CH3O | |
| 5-Br | O | H | H | H | H | N | CH3O | CH3O | |
| 5-CH3 | O | H | H | H | H | N | CH3O | CH3O | |
| 5-CH3O | O | H | H | H | H | N | CH3O | CH3O | |
| 5-CF3 | O | H | H | H | H | N | CH3O | CH3O | |
| 5-Cl | O | H | H | H | H | N | CH3O | CH3O | |
| H | O | H | H | H | H | CH | Cl | CH3O | |
| H | O | H | H | H | H | CH | CH3 | CH2OCH3 | |
| H | O | H | H | H | H | CH | CH3 | CH(OCH3)2 | |
| H | O | H | H | H | H | N | CH3 | C2H5O | |
| H | O | H | H | H | H | N | CH3O | N(CH3)2 | |
| H | O | H | H | H | H | CH | Cl | NH2 | |

TABLE 5

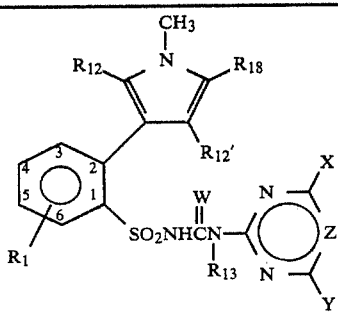

| R1 | W | R12 | R12' | R13 | R18 | Z | X | Y | m.p. (°C.) |
|---|---|---|---|---|---|---|---|---|---|
| H | O | H | H | H | H | CH | CH3O | CH3O | |
| H | O | H | H | H | H | CH | CH3O | CH3 | |
| H | O | H | H | H | H | CH | CH3 | CH3 | |
| H | O | H | H | H | H | N | CH3O | CH3O | |
| H | O | H | H | H | H | N | CH3O | CH3 | |
| H | O | CH3 | H | H | CH3 | CH | CH3O | CH3O | |
| H | O | CH3 | H | H | CH3 | CH | CH3O | CH3 | |
| H | S | CH3 | H | H | CH3 | N | CH3O | CH3O | |
| H | S | CH3 | H | H | CH3 | N | CH3O | CH3 | |
| H | O | CH3 | CH3 | H | CH3 | N | CH3O | CH3 | |
| H | O | H | H | CH3 | H | N | CH3O | CH3O | |
| H | O | H | CH3 | H | H | N | CH3O | CH3 | |
| H | O | H | H | H | CH3 | N | CH3O | CH3 | |
| 5-F | O | H | H | H | H | N | CH3O | CH3 | |
| 3-Br | O | H | H | H | H | N | CH3O | CH3 | |
| 4-CH3 | O | H | H | H | H | N | CH3O | CH3 | |
| 6-Cl | O | H | H | H | H | N | CH3O | CH3 | |
| 5-CF3 | O | H | H | H | H | N | CH3O | CH3 | |
| 5-CH3O | O | H | H | H | H | N | CH3O | CH3 | |
| H | O | H | H | H | H | CH | Cl | CH3O | |
| H | O | H | H | H | H | CH | CH3 | CH(OCH3)2 | |
| H | O | H | H | H | H | CH | CH3O | CH2OCH3 | |
| H | O | H | H | H | H | N | CH3O | N(CH3)2 | |
| H | O | H | H | H | H | N | CH3 | NHCH3 | |
| H | O | H | H | H | H | N | CH3O | NH2 | |
| H | S | H | H | H | H | CH | CH3 | CH(—OCH2CH2O—) | |
| H | O | H | H | H | H | CH | OCH3 | CF3 | |

TABLE 6

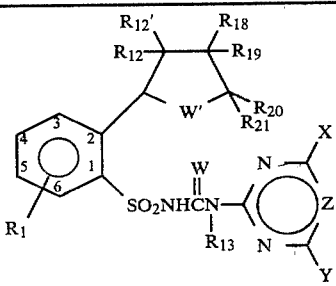

| R1 | W | R13 | R12 | R12' | R18 | R19 | R20 | R21 | W' | Z | X | Y | m.p. (°C.) |
|---|---|---|---|---|---|---|---|---|---|---|---|---|---|
| H | O | H | H | H | H | H | H | H | O | CH | CH3O | CH3O | |
| H | O | H | H | H | H | H | H | H | O | CH | CH3O | CH3 | |
| H | O | H | H | H | H | H | H | H | O | CH | CH3 | CH3 | |
| H | O | H | H | H | H | H | H | H | O | N | CH3O | CH3O | |
| H | O | H | H | H | H | H | H | H | O | N | CH3O | CH3 | |
| H | O | H | H | H | H | H | H | H | O | N | CH3 | CH3 | |
| H | O | H | H | H | H | H | H | H | S | CH | CH3O | CH3O | |
| H | O | H | H | H | H | H | H | H | S | CH | CH3O | CH3 | |
| H | O | H | H | H | H | H | H | H | S | CH | CH3 | CH3 | |
| H | O | H | H | H | H | H | H | H | S | N | CH3O | CH3O | |
| H | S | H | H | H | H | H | H | H | S | N | CH3O | CH3 | |
| H | O | H | H | H | H | H | H | H | S | N | CH3 | CH3 | |
| H | O | CH3 | H | H | H | H | H | H | O | N | CH3O | CH3O | |
| H | O | H | CH3 | CH3 | H | H | H | H | O | N | CH3O | CH3 | |
| H | O | H | H | H | CH3 | CH3 | H | H | O | N | CH3O | CH3 | |
| H | O | H | H | H | H | H | CH3 | CH3 | O | N | CH3O | CH3 | |
| H | O | H | CH3 | H | CH3 | H | CH3 | H | O | N | CH3O | CH3 | |

TABLE 6-continued

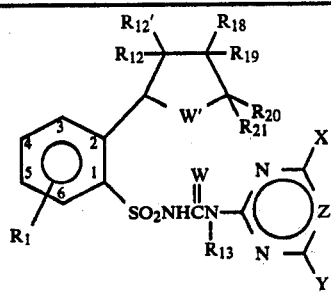

| R₁ | W | R₁₃ | R₁₂ | R₁₂' | R₁₈ | R₁₉ | R₂₀ | R₂₁ | W' | Z | X | Y | m.p. (°C.) |
|---|---|---|---|---|---|---|---|---|---|---|---|---|---|
| H | O | H | CH₃ | H | H | H | H | H | O | N | CH₃O | CH₃ | |
| H | O | H | H | H | CH₃ | H | H | H | O | N | CH₃O | CH₃ | |
| H | O | H | H | H | H | H | CH₃ | H | O | N | CH₃O | CH₃ | |
| H | O | H | CH₃ | H | CH₃ | H | CH₃ | CH₃ | O | N | CH₃O | CH₃ | |
| 5-F | O | H | H | H | H | H | H | H | O | N | CH₃O | CH₃ | |
| 3-Br | O | H | H | H | H | H | H | H | O | N | CH₃O | CH₃ | |
| 4-CH₃ | O | H | H | H | H | H | H | H | O | N | CH₃O | CH₃ | |
| 6-Cl | O | H | H | H | H | H | H | H | O | N | CH₃O | CH₃ | |
| 5-CF₃ | O | H | H | H | H | H | H | H | O | N | CH₃O | CH₃ | |
| 5-CH₃ | O | H | H | H | H | H | H | H | O | N | CH₃O | CH₃ | |
| 5-CH₃O | O | H | H | H | H | H | H | H | O | N | CH₃O | CH₃ | |
| 5-Cl | O | H | H | H | H | H | H | H | O | N | CH₃O | CH₃ | |
| H | O | H | H | H | H | H | H | H | O | CH | Cl | CH₃O | |
| H | O | H | H | H | H | H | H | H | O | CH | CH₃ | CH(OCH₃)₂ | |
| H | S | H | H | H | H | H | H | H | O | CH | CH₃O | —CH₂OCH₃ | |
| H | O | H | H | H | H | H | H | H | O | N | CH₃O | N(CH₃)₂ | |
| H | O | H | H | H | H | H | H | H | O | N | CH₃O | NHCH₃ | |
| H | O | H | H | H | H | H | H | H | O | N | CH₃ | NH₂ | |
| H | O | H | H | H | H | H | H | H | O | N | CH₃ | C₂H₅O— | |
| H | O | H | H | H | H | H | H | H | O | N | CH₃O | C₂H₅— | |
| H | O | H | H | H | H | H | H | H | O | CH | CH₃ | OCH₂CH₂OCH₃ | |

TABLE 7

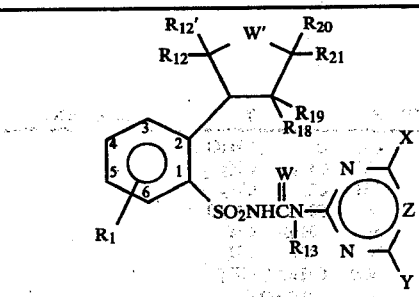

| R₁ | W | R₁₃ | R₁₂ | R₁₂' | R₁₈ | R₁₉ | R₂₀ | R₂₁ | W' | Z | X | Y | m.p. (°C.) |
|---|---|---|---|---|---|---|---|---|---|---|---|---|---|
| H | O | H | H | H | H | H | H | H | O | CH | CH₃O | CH₃O | 183–185° |
| H | O | H | H | H | H | H | H | H | O | CH | CH₃O | CH₃ | 185–186° |
| H | S | H | H | H | H | H | H | H | O | CH | CH₃ | CH₃ | |
| H | O | H | H | H | H | H | H | H | O | N | CH₃O | CH₃O | 171–180° |
| H | O | H | H | H | H | H | H | H | O | N | CH₃O | CH₃ | 181–186° (d) |
| H | O | H | H | H | H | H | H | H | O | N | CH₃ | CH₃ | |
| H | O | CH₃ | H | H | H | H | H | H | O | N | CH₃ | CH₃ | |
| H | O | H | H | H | H | H | H | H | S | CH | CH₃O | CH₃O | |
| H | O | H | H | H | H | H | H | H | S | CH | CH₃O | CH₃ | |
| H | S | H | H | H | H | H | H | H | S | CH | CH₃ | CH₃ | |
| H | O | H | H | H | H | H | H | H | S | N | CH₃O | CH₃O | |
| H | O | H | H | H | H | H | H | H | S | N | CH₃O | CH₃ | |
| H | O | H | H | H | H | H | H | H | S | N | CH₃ | CH₃ | |
| H | O | H | CH₃ | CH₃ | H | H | H | H | O | N | CH₃O | CH₃ | |
| H | O | H | H | H | H | CH₃ | CH₃ | H | O | N | CH₃O | CH₃ | |
| H | O | H | CH₃ | H | CH₃ | H | CH₃ | H | O | N | CH₃O | CH₃ | |
| H | O | H | CH₃ | CH₃ | H | H | CH₃ | CH₃ | O | N | CH₃O | CH₃ | |
| 5-F | O | H | H | H | H | H | H | H | O | N | CH₃O | CH₃ | |
| 5-Br | O | H | H | H | H | H | H | H | O | N | CH₃O | CH₃ | |
| 5-CH₃ | O | H | H | H | H | H | H | H | O | N | CH₃O | CH₃ | |
| 5-CF₃ | O | H | H | H | H | H | H | H | O | N | CH₃O | CH₃ | |
| 5-Cl | O | H | H | H | H | H | H | H | O | N | CH₃O | CH₃ | |
| H | O | H | H | H | H | H | H | H | O | CH | CH₃ | CH₃ | 184–187° |
| 5-CH₃O | O | H | H | H | H | H | H | H | O | N | CH₃O | CH₃ | |

TABLE 7-continued

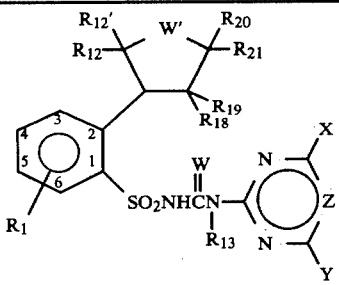

| R$_1$ | W | R$_{13}$ | R$_{12}$ | R$_{12'}$ | R$_{18}$ | R$_{19}$ | R$_{20}$ | R$_{21}$ | W' | Z | X | Y | m.p. (°C.) |
|---|---|---|---|---|---|---|---|---|---|---|---|---|---|
| 3-Cl | O | H | H | H | H | H | H | H | O | N | CH$_3$O | CH$_3$ | |
| 4-Cl | O | H | H | H | H | H | H | H | O | N | CH$_3$O | CH$_3$ | |
| 6-Cl | O | H | H | H | H | H | H | H | O | N | CH$_3$O | CH$_3$ | |
| H | O | H | H | H | H | H | H | H | O | CH | Cl | CH$_3$O | |
| H | O | H | H | H | H | H | H | H | O | CH | CH$_3$O | CH$_2$OCH$_3$ | |
| H | O | H | H | H | H | H | H | H | O | CH | CH$_3$O | CH(OCH$_3$)$_2$ | |
| H | O | H | H | H | H | H | H | H | O | N | CH$_3$O | N(CH$_3$)$_2$ | |
| H | O | H | H | H | H | H | H | H | O | N | CH$_3$ | NHCH$_3$ | |
| H | O | H | H | H | H | H | H | H | O | N | CH$_3$O | NH$_2$ | |
| H | O | H | H | H | H | H | H | H | O | N | CH$_3$ | C$_2$H$_5$O | |
| H | O | H | H | H | H | H | H | H | O | N | CH$_3$O | C$_2$H$_5$ | |
| H | O | H | H | H | H | H | H | H | O | N | CH$_3$ | OCH$_2$CF$_3$ | |

TABLE 8

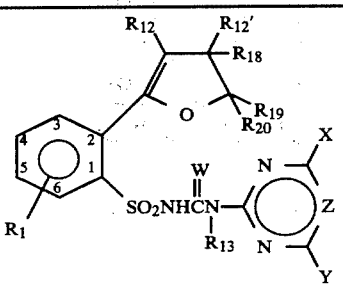

| R$_1$ | W | R$_{13}$ | R$_{12}$ | R$_{12'}$ | R$_{18}$ | R$_{19}$ | R$_{20}$ | R$_{21}$ | W' | Z | X | Y | m.p. (°C.) |
|---|---|---|---|---|---|---|---|---|---|---|---|---|---|
| H | O | H | H | H | H | H | H | | | CH | O | CH$_3$O | |
| H | O | H | H | H | H | H | H | | | CH | CH$_3$O | CH$_3$ | |
| H | O | H | H | H | H | H | H | | | CH | CH$_3$ | CH$_3$ | |
| H | O | H | H | H | H | H | H | | | N | CH$_3$O | CH$_3$O | |
| H | O | H | H | H | H | H | H | | | N | CH$_3$O | CH$_3$ | |
| H | O | H | H | H | H | H | H | | | N | CH$_3$ | CH$_3$ | |
| H | O | CH$_3$ | H | H | H | H | H | | | N | CH$_3$O | CH$_3$ | |
| H | S | H | CH$_3$ | H | H | H | H | | | N | CH$_3$O | CH$_3$ | |
| H | O | H | CH$_3$ | CH$_3$ | H | H | H | | | N | CH$_3$O | CH$_3$ | |
| H | O | H | CH$_3$ | CH$_3$ | CH$_3$ | H | H | | | N | CH$_3$O | CH$_3$ | |
| H | O | H | H | H | H | CH$_3$ | CH$_3$ | | | N | CH$_3$O | CH$_3$ | |
| H | O | H | CH$_3$ | H | CH$_3$ | H | H | | | N | CH$_3$O | CH$_3$ | |
| H | O | H | CH$_3$ | CH$_3$ | CH$_3$ | CH$_3$ | CH$_3$ | | | N | CH$_3$O | CH$_3$ | |
| H | O | H | CH$_3$ | CH$_3$ | H | CH$_3$ | CH$_3$ | | | N | CH$_3$O | CH$_3$ | |
| 5-F | O | H | H | H | H | H | H | | | N | CH$_3$O | CH$_3$ | |
| 5-Cl | O | H | H | H | H | H | H | | | N | CH$_3$O | CH$_3$ | |
| 5-CH$_3$ | O | H | H | H | H | H | H | | | N | CH$_3$O | CH$_3$ | |
| 5-Br | O | H | H | H | H | H | H | | | N | CH$_3$O | CH$_3$ | |
| 5-CF$_3$ | O | H | H | H | H | H | H | | | N | CH$_3$O | CH$_3$ | |
| 5-CH$_3$O | O | H | H | H | H | H | H | | | N | CH$_3$O | CH$_3$ | |
| 3-Cl | O | H | H | H | H | H | H | | | N | CH$_3$O | CH$_3$ | |
| 4-Cl | O | H | H | H | H | H | H | | | N | CH$_3$O | CH$_3$ | |
| 6-Cl | O | H | H | H | H | H | H | H | O | N | CH$_3$O | CH$_3$ | |
| H | O | H | H | H | H | H | H | H | O | CH | Cl | CH$_3$O | |
| H | O | H | H | H | H | H | H | H | O | CH | Cl | NH$_2$ | |
| H | O | H | H | H | H | H | H | H | O | CH | CH$_3$ | CH$_2$OCH$_3$ | |
| H | O | H | H | H | H | H | H | H | O | CH | CH$_3$O | CH(OCH$_3$)$_2$ | |
| H | O | H | H | H | H | H | H | H | O | N | CH$_3$O | N(CH$_3$)$_2$ | |
| H | O | H | H | H | H | H | H | H | O | N | CH$_3$ | NH$_2$ | |
| H | O | H | H | H | H | H | H | H | O | N | CH$_3$O | C$_2$H$_5$O | |
| H | S | H | H | H | H | H | H | H | O | N | CH$_3$O | C$_2$H$_5$ | |
| H | O | H | H | H | H | H | H | H | O | N | CH$_3$O | NH(CH$_3$)$_2$ | |

TABLE 9

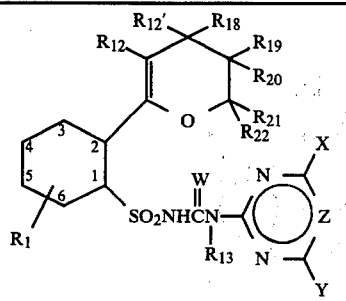

| R1 | W | R13 | R12 | R12' | R18 | R19 | R20 | R21 | R22 | Z | X | Y | m.p. (°C.) |
|---|---|---|---|---|---|---|---|---|---|---|---|---|---|
| H | O | H | H | H | H | H | H | H | H | CH | $CH_3O$ | $CH_3O$ | |
| H | S | H | H | H | H | H | H | H | H | CH | $CH_3O$ | $CH_3$ | |
| H | O | H | H | H | H | H | H | H | H | CH | $CH_3$ | $CH_3$ | |
| H | O | H | H | H | H | H | H | H | H | N | $CH_3O$ | $CH_3O$ | |
| H | O | H | H | H | H | H | H | H | H | N | $CH_3O$ | $CH_3$ | |
| H | O | H | H | H | H | H | H | H | H | N | $CH_3$ | $CH_3$ | |
| H | O | $CH_3$ | H | H | H | H | H | H | H | N | $CH_3O$ | $CH_3O$ | |
| H | O | H | $CH_3$ | H | H | H | H | H | H | N | $CH_3O$ | $CH_3$ | |
| H | O | H | H | $CH_3$ | $CH_3$ | H | H | H | H | N | $CH_3O$ | $CH_3$ | |
| H | O | H | H | H | H | $CH_3$ | $CH_3$ | H | H | N | $CH_3O$ | $CH_3$ | |
| H | O | H | H | H | H | H | H | $CH_3$ | $CH_3$ | N | $CH_3O$ | $CH_3$ | |
| H | O | H | $CH_3$ | H | H | H | H | $CH_3$ | $CH_3$ | N | $CH_3O$ | $CH_3$ | |
| H | S | H | $CH_3$ | $CH_3$ | H | $CH_3$ | H | $CH_3$ | H | N | $CH_3O$ | $CH_3$ | |
| 5-Cl | O | H | H | H | H | H | H | H | H | N | $CH_3O$ | $CH_3$ | |
| 5-F | O | H | H | H | H | H | H | H | H | N | $CH_3O$ | $CH_3$ | |
| 5-$CH_3$ | O | H | H | H | H | H | H | H | H | N | $CH_3O$ | $CH_3$ | |
| 5-Br | O | H | H | H | H | H | H | H | H | N | $CH_3O$ | $CH_3$ | |
| 5-$CF_3$ | O | H | H | H | H | H | H | H | H | N | $CH_3O$ | $CH_3$ | |
| 5-$CH_3O$ | O | H | H | H | H | H | H | H | H | N | $CH_3O$ | $CH_3$ | |
| 3-Cl | O | H | H | H | H | H | H | H | H | N | $CH_3O$ | $CH_3$ | |
| 4-Cl | O | H | H | H | H | H | H | H | H | N | $CH_3O$ | $CH_3$ | |
| 6-Cl | O | H | H | H | H | H | H | H | H | N | $CH_3O$ | $CH_3$ | |
| H | O | H | H | H | H | H | H | H | H | CH | Cl | $CH_3O$ | |
| H | O | H | H | H | H | H | H | H | H | CH | Cl | $NH_2$ | |
| H | O | H | H | H | H | H | H | H | H | CH | $CH_3$ | $CH_2OCH_3$ | |
| H | O | H | H | H | H | H | H | H | H | CH | $CH_3$ | $CH(OCH_3)_2$ | |
| H | O | H | H | H | H | H | H | H | H | N | $CH_3O$ | $N(CH_3)_2$ | |
| H | O | H | H | H | H | H | H | H | H | N | $CH_3$ | $NH_2$ | |
| H | O | H | H | H | H | H | H | H | H | N | $CH_3O$ | $NHCH_3$ | |
| H | O | H | H | H | H | H | H | H | H | N | $CH_3O$ | $C_2H_5O$ | |
| H | O | H | H | H | H | H | H | H | H | N | $CH_3O$ | $C_2H_5$ | |
| H | O | H | H | H | H | H | H | H | H | CH | $CH_3$ | $SCH_3$ | |

TABLE 10

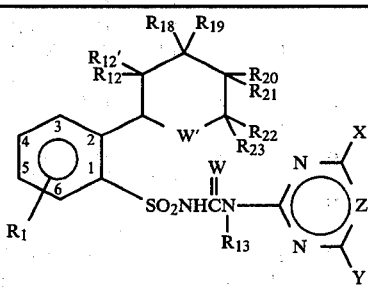

| R1 | W | W' | R12 | R12' | R13 | R18 | R19 | R20 | R21 | R22 | R23 | Z | X | Y | m.p. (°C.) |
|---|---|---|---|---|---|---|---|---|---|---|---|---|---|---|---|
| H | O | O | H | H | H | H | H | H | H | H | H | CH | $CH_3$ | $CH_3$ | |
| H | O | O | H | H | H | H | H | H | H | H | H | CH | $CH_3$ | $OCH_3$ | |
| H | O | O | H | H | H | H | H | H | H | H | H | CH | $OCH_3$ | $OCH_3$ | |
| H | O | O | H | H | H | H | H | H | H | H | H | N | $CH_3$ | $OCH_3$ | |
| H | S | O | H | H | H | H | H | H | H | H | H | N | $OCH_3$ | $OCH_3$ | |
| H | O | O | H | H | H | H | H | H | H | H | H | N | $OCH_3$ | $OCH_3$ | |
| H | O | S | H | H | $CH_3$ | H | H | H | H | H | H | N | $CH_3$ | $OCH_3$ | |
| H | S | S | H | H | H | H | H | H | H | H | H | CH | Cl | $OCH_3$ | |
| H | O | S | H | H | H | H | H | H | H | H | H | CH | $OCH_3$ | $CF_3$ | |
| H | O | S | H | H | H | H | $CH_3$ | H | H | H | H | CH | $CH_3$ | $SCH_3$ | |
| H | O | O | $CH_3$ | $CH_3$ | H | H | H | H | H | H | H | N | $CH_3$ | $OCH_2CF_3$ | |
| H | O | O | $CH_3$ | H | H | $CH_3$ | H | H | H | H | H | N | $OCH_3$ | $OC_2H_5$ | |

TABLE 10-continued

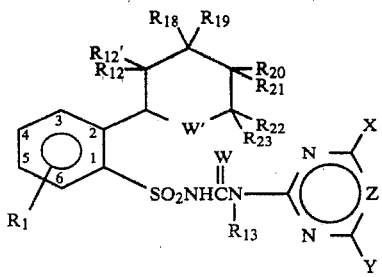

| R₁ | W | W' | R₁₂ | R₁₂' | R₁₃ | R₁₈ | R₁₉ | R₂₀ | R₂₁ | R₂₂ | R₂₃ | Z | X | Y | m.p. (°C.) |
|---|---|---|---|---|---|---|---|---|---|---|---|---|---|---|---|
| H | O | O | H | H | H | H | H | CH₃ | H | H | H | N | OCH₃ | CH₃ | |
| H | O | O | CH₃ | CH₃ | H | H | H | H | H | CH₃ | CH₃ | CH | CH₃ | C₂H₅ | |
| H | O | O | H | H | H | H | H | H | CH₃ | H | H | CH | OCH₃ | CH₃ | |
| H | O | O | H | H | H | H | H | H | CH₃ | H | H | CH | CH₃ | CH₃ | |
| H | O | O | H | H | H | H | H | H | H | H | H | N | OCH₃ | OCH₂CH₂OCH₃ | |
| H | O | S | H | H | H | H | H | H | H | H | H | N | CH₃ | OCH₃ | |
| H | O | S | H | H | H | H | H | H | H | H | H | N | CH₃ | CH(—OCH₂CH₂O—) | |
| 5-Cl | O | O | H | H | H | H | H | H | H | H | H | CH | OCH₃ | CH₃ | |
| 5-CH₃ | O | O | H | H | H | H | H | H | H | H | H | CH | Cl | OCH₃ | |
| 6-Cl | O | O | H | H | H | H | H | H | H | H | H | CH | OCH₃ | CH₂OCH₃ | |
| 4-CH₃ | O | O | H | H | H | H | H | H | H | H | H | CH | CH₃ | OCH₃ | |

TABLE 11

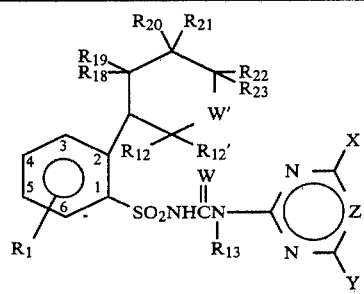

| R₁ | W | W' | R₁₂ | R₁₂' | R₁₃ | R₁₈ | R₁₉ | R₂₀ | R₂₁ | R₂₂ | R₂₃ | Z | X | Y | m.p. (°C.) |
|---|---|---|---|---|---|---|---|---|---|---|---|---|---|---|---|
| H | O | O | O | H | H | H | H | H | H | H | H | CH | CH₃ | CH₃ | |
| H | O | O | H | H | H | H | H | H | H | H | H | CH | CH₃ | OCH₃ | |
| H | O | O | H | H | H | H | H | H | H | H | H | CH | OCH₃ | OCH₃ | |
| H | O | O | H | H | H | H | H | H | H | H | H | N | CH₃ | OCH₃ | |
| H | S | O | H | H | H | H | H | H | H | H | H | N | OCH₃ | OCH₃ | |
| H | O | O | H | H | H | H | H | H | H | H | H | N | OCH₃ | OCH₃ | |
| H | O | S | H | H | CH₃ | H | H | H | H | H | H | N | CH₃ | OCH₃ | |
| H | S | S | H | H | H | H | H | H | H | H | H | CH | Cl | OCH₃ | |
| H | O | S | H | H | H | H | H | H | H | H | H | CH | OCH₃ | CF₃ | |
| H | O | S | H | H | H | H | CH₃ | H | H | H | H | CH | CH₃ | SCH₃ | |
| H | O | O | CH₃ | CH₃ | H | H | H | H | H | H | H | N | CH₃ | OCH₂CF₃ | |
| H | O | O | CH₃ | H | H | CH₃ | H | H | H | H | H | N | OCH₃ | OC₂H₅ | |
| H | O | O | H | H | H | H | H | CH₃ | H | H | H | N | OCH₃ | CH₃ | |
| H | O | O | CH₃ | CH₃ | H | H | H | H | H | CH₃ | CH₃ | CH | CH₃ | C₂H₅ | |
| H | O | O | H | H | H | H | H | H | CH₃ | H | H | CH | OCH₃ | CH₃ | |
| H | O | O | H | H | H | H | H | H | CH₃ | H | H | CH | CH₃ | CH₃ | |
| H | O | O | H | H | H | H | H | H | H | H | H | N | OCH₃ | OCH₂CH₂OCH₃ | |
| H | O | S | H | H | H | H | H | H | H | H | H | N | CH₃ | OCH₃ | |
| H | O | S | H | H | H | H | H | H | H | H | H | N | CH₃ | CH(—OCH₂CH₂O—) | |
| 5-Cl | O | O | H | H | H | H | H | H | H | H | H | CH | OCH₃ | CH₃ | |
| 5-CH₃ | O | O | H | H | H | H | H | H | H | H | H | CH | Cl | OCH₃ | |
| 6-Cl | O | O | H | H | H | H | H | H | H | H | H | CH | OCH₃ | CH₂OCH₃ | |
| 4-CH₃ | O | O | H | H | H | H | H | H | H | H | H | CH | CH₃ | OCH₃ | |

TABLE 12

| Q | R₁ | R₁₃ | X₁ | G | m.p.(°C) |
|---|----|----|----|----|----|
| furan-2-yl | H | H | CH₃ | CH₂ | |
| thiophen-2-yl | H | H | CH₃ | O | |
| tetrahydrofuran-2-yl | H | H | CH₃ | O | |
| tetrahydrofuran-3-yl | H | H | CH₃ | O | |
| N-pyrrolyl | H | H | CH₃ | O | |
| 1-methylpyrrol-2-yl | H | H | OCH₃ | O | |
| 1-methylpyrrol-3-yl | H | H | OCH₃ | CH₂ | |
| thiophen-3-yl | 5-Cl | H | CH₃ | O | |
| 2,3-dihydrofuran-5-yl | H | H | CH₃ | O | |
| 3,4-dihydro-2H-pyran-6-yl | H | CH₃ | CH₃ | O | |
| tetrahydropyran-2-yl | H | H | Cl | O | |
| tetrahydropyran-2-yl (S) | H | H | CH₃ | O | |
| tetrahydropyran-3-yl (S) | H | H | CH₃ | O | |
| tetrahydropyran-3-yl (O) | H | H | CH₃ | CH₂ | |
| 5-methylfuran-2-yl | H | H | CH₃ | O | |
| 5-methoxycarbonylfuran-2-yl | H | H | CH₃ | O | |
| 5-methylthiophen-2-yl | H | H | CH₃ | O | |
| 2,2-dimethyltetrahydrothiophen-5-yl | H | H | CH₃ | O | |

TABLE 13

| Q | R₁ | R₁₃ | X₁ | m.p.(°C) |
|---|----|----|----|----|
| furan-2-yl | H | H | CH₃ | |
| thiophen-2-yl | H | H | CH₃ | |
| tetrahydrofuran-2-yl | H | H | CH₃ | |

TABLE 13-continued
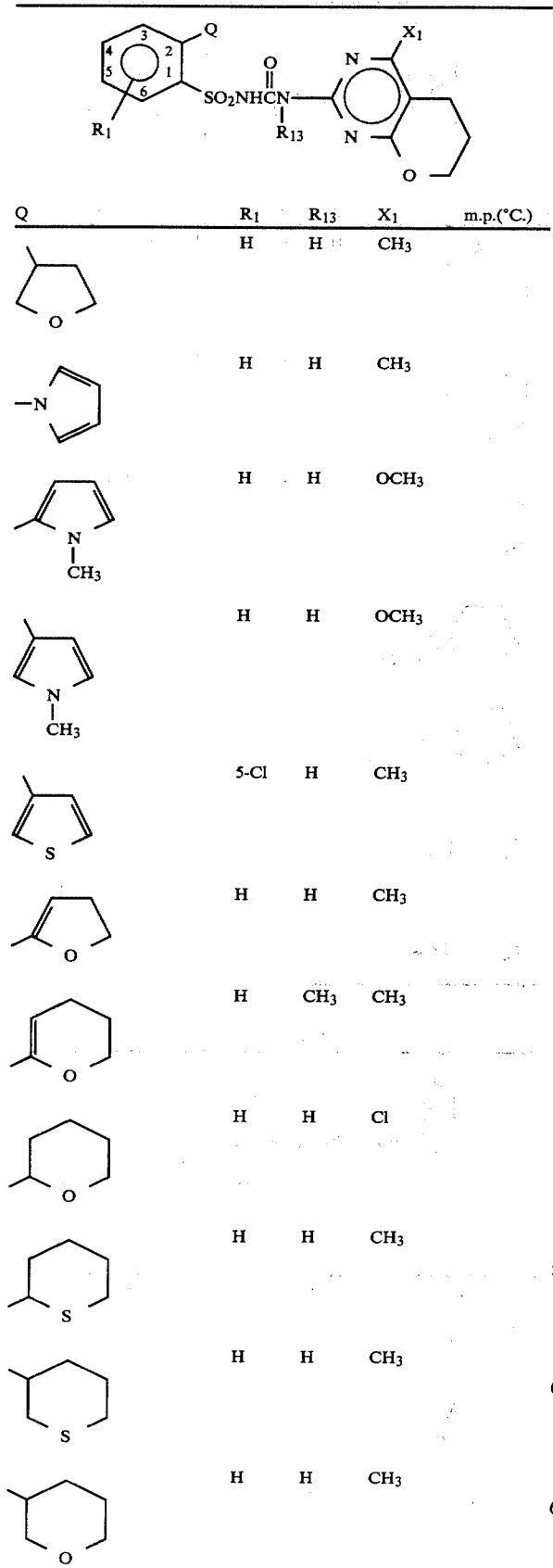
TABLE 14
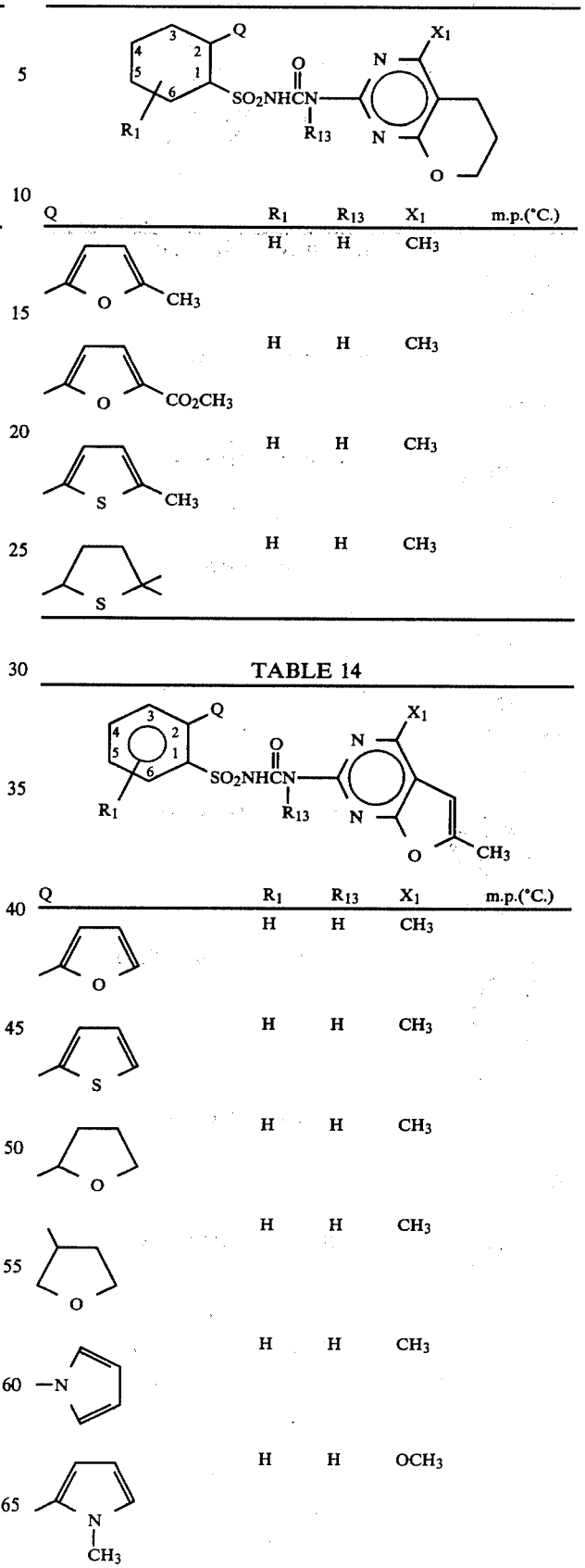

TABLE 14-continued

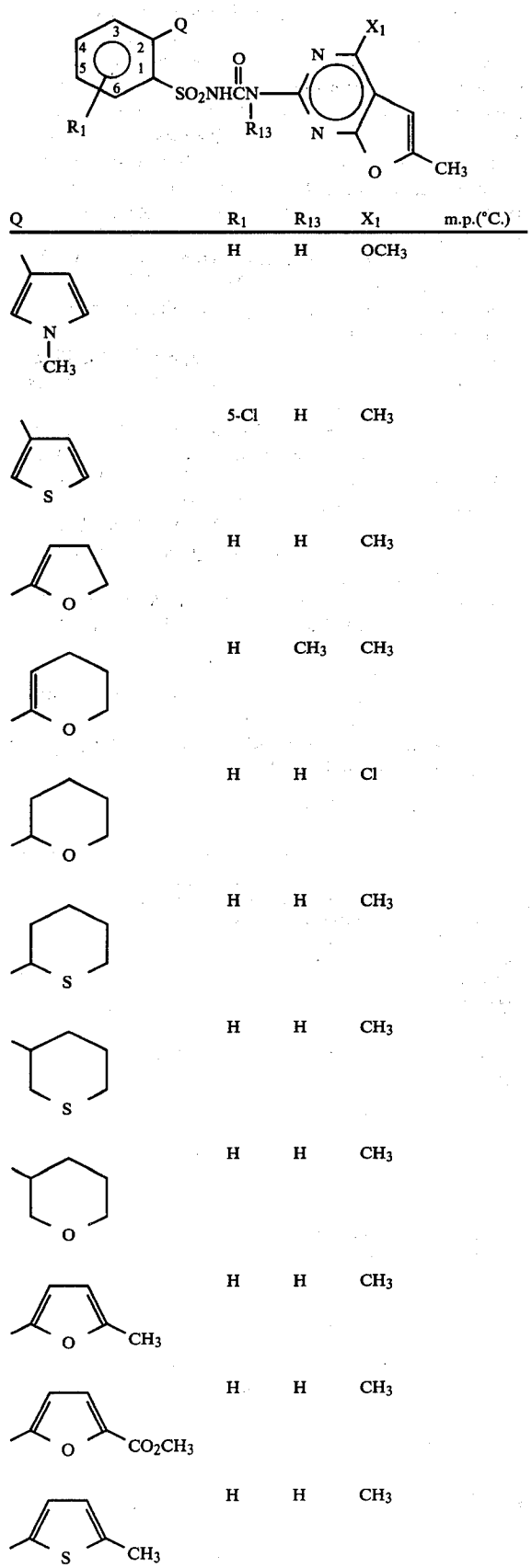

| Q | R₁ | R₁₃ | X₁ | m.p.(°C.) |
|---|----|----|----|-----------|
| 4-methyl-N-methylpyrrol-1-yl | H | H | OCH₃ | |
| 3-methylthien-2-yl | 5-Cl | H | CH₃ | |
| 5-methyl-2,3-dihydrofuran-2-yl | H | H | CH₃ | |
| 6-methyl-3,4-dihydro-2H-pyran-6-yl | H | CH₃ | CH₃ | |
| 6-methyltetrahydropyran-2-yl | H | H | Cl | |
| 2-methyltetrahydrothiopyran-2-yl | H | H | CH₃ | |
| 3-methyltetrahydrothiopyran-3-yl | H | H | CH₃ | |
| 3-methyltetrahydropyran-3-yl | H | H | CH₃ | |
| 2,5-dimethylfuran-2-yl | H | H | CH₃ | |
| 5-CO₂CH₃-2-methylfuran-2-yl | H | H | CH₃ | |
| 5-methyl-2-methylthien-2-yl | H | H | CH₃ | |

TABLE 14-continued

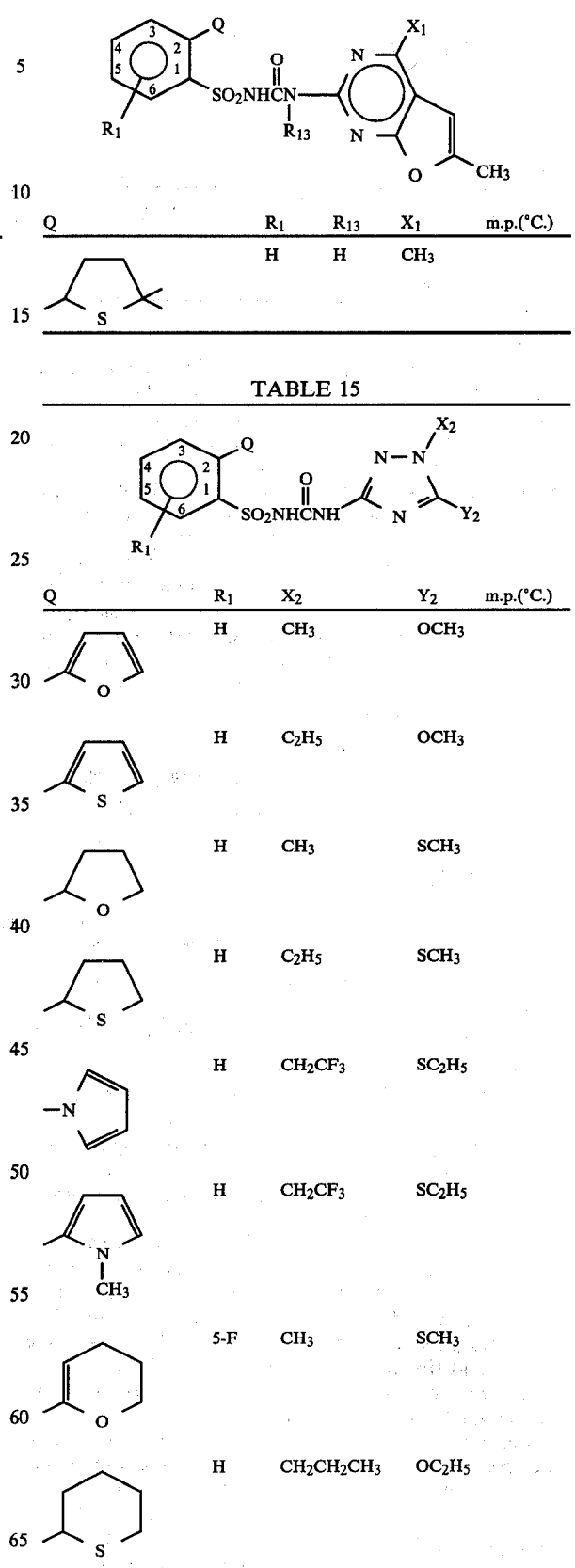

| Q | R₁ | R₁₃ | X₁ | m.p.(°C.) |
|---|----|----|----|-----------|
| 2,2,5-trimethyltetrahydrothien-5-yl | H | H | CH₃ | |

TABLE 15

| Q | R₁ | X₂ | Y₂ | m.p.(°C.) |
|---|----|----|----|-----------|
| 2-methylfuran-2-yl | H | CH₃ | OCH₃ | |
| 5-methylthien-2-yl | H | C₂H₅ | OCH₃ | |
| 2-methyltetrahydrofuran-2-yl | H | CH₃ | SCH₃ | |
| 2-methyltetrahydrothien-2-yl | H | C₂H₅ | SCH₃ | |
| pyrrol-1-yl | H | CH₂CF₃ | SC₂H₅ | |
| 2-methyl-N-methylpyrrol-2-yl | H | CH₂CF₃ | SC₂H₅ | |
| 6-methyl-3,4-dihydro-2H-pyran-6-yl | 5-F | CH₃ | SCH₃ | |
| 2-methyltetrahydrothiopyran-2-yl | H | CH₂CH₂CH₃ | OC₂H₅ | |

TABLE 15-continued (structure: benzene ring numbered 1-6 with Q at position 2, R₁ at position 5, SO₂NHCNH-C(=O)-N=N with X₂ branch and Y₂ on pyrimidine-like ring)

| Q | R₁ | X₂ | Y₂ | m.p.(°C.) |
|---|----|----|----|-----------|
| (tetrahydropyran-2-yl with CH₃) | H | C₂H₅ | OCH₃ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 16

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley & Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 5

| Wettable Powder | |
|---|---|
| 2-(2-Carbomethoxyfur-5-yl)-N—[(4,6-dimethoxypyrimidin-2-yl)aminocarbonyl]benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

Example 6

| Wettable Powder | |
|---|---|
| N—[(4-methoxy-6-methylpyrimidin-2-yl)aminocarbonyl]-2-(tetrahydrofuran-2-yl)benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

Example 7

| Granule | |
|---|---|
| Wettable Powder of Example 9 | 5% |

| Granule | |
|---|---|
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

Example 8

| Extruded Pellet | |
|---|---|
| N—[(4,6-dimethoxypyrimidin-2-yl)aminocarbonyl]-2-(tetrahydrofuran-2-yl)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

Example 9

| Oil Suspension | |
|---|---|
| N—[(4-chloro-6-methoxypyrimidin-2-yl)aminocarbonyl]-2-(tetrahydrofuran-2-yl)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

Example 10

| Wettable Powder | |
|---|---|
| N—[(4,6-dimethoxy-1,3,5-triazin-2-yl)aminocarbonyl]-2-(tetrahydrofuran-2-yl)benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Example 11

| Low Strength Granule | |
|---|---|
| N—[(4,6-dimethylpyrimidin-2-yl)aminocarbonyl]-2-(tetrahydrofuran-2-yl)benzenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

Example 12

| Aqueous Suspension | |
|---|---|
| N—[(4-methoxy-6-methylpyrimidin-2-yl)aminocarbonyl]-2-(tetrahydrofuran-2-yl)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

Example 13

| Solution | |
|---|---|
| N—[(4-methoxy-6-methyl-1,3,5-triazin-2-yl)aminocarbonyl]-2-(tetrahydrofuran-2-yl)benzenesulfonamide, sodium salt | 5% |
| water | 95% |

The salt is added directly to the water with stirring to produce the solution, which may then be packaged for use.

Example 14

| Low Strength Granule | |
|---|---|
| N—[(4-chloro-6-methoxypyrimidin-2-yl)aminocarbonyl]-2-(tetrahydrofuran-2-yl)benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

Example 15

| Granule | |
|---|---|
| N—[(4,6-dimethoxypyrimidin-2-yl)aminocarbonyl]-2-(tetrahydrofuran-2-yl)benzenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410-149 microns), and packaged for use.

Example 16

| High Strength Concentrate | |
|---|---|
| 2-(2-Carbomethoxyfur-5-yl)-N—[(4,6-dimethyl-1,3,5-triazin-2-yl)aminocarbonyl]benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

Example 17

| Wettable Powder | |
|---|---|
| N—[(4,6-dimethoxy-1,3,5-triazin-2-yl)aminocarbonyl]-2-(tetrahydrofuran-2-yl)benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

Example 18

| Wettable Powder | |
|---|---|
| N—[(4,6-dimethylpyrimidin-2-yl)aminocarbonyl]-2-(tetrahydrofuran-2-yl)benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

Example 19

| Oil Suspension | |
|---|---|
| N—[(4-methoxy-6-methylpyrimidin-2-yl)aminocarbonyl]-2-(tetrahydrofuran-2-yl)benzenesulfonamide | 35% |
| blend of polyalcohol carboxylic esters and oil soluble pertoleum sulfonates | 6% |
| xylene | 59% |

The ingredients are combined and ground together in a sand mill to produce particles essentially all below 5 microns. The product can be used directly, extended with oils, or emulsified in water.

Example 20

| Dust | |
|---|---|
| N—[(4,6-dimethoxypyrimidin-2-yl)aminocarbonyl]-2- | 10% |

-continued

| Dust | |
|---|---|
| (tetrahydrofuran-2-yl)benzenesulfonamide | |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

The compounds of the present invention are powerful herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for the selective pre- or post-emergence weed control in crops, such as wheat, barley and corn.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.01 to 5 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results follow.

Compounds

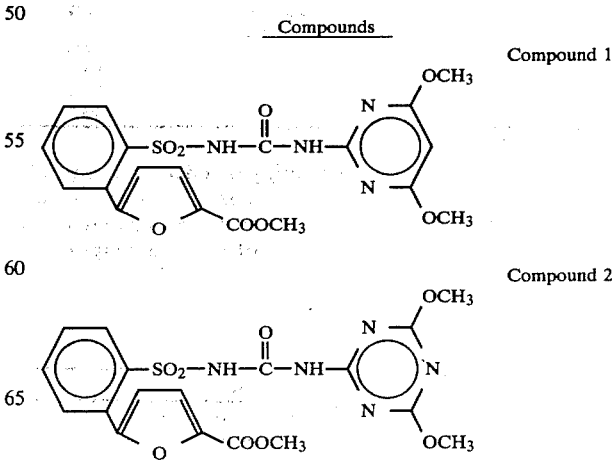

-continued
Compounds
Compound 3
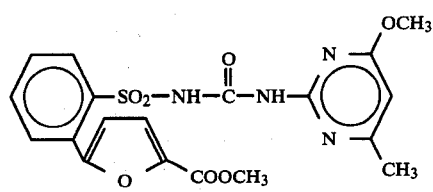
Compound 4
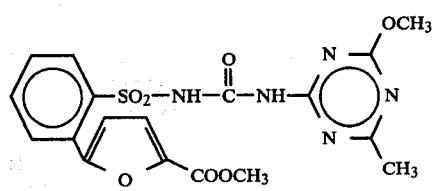
Compound 5
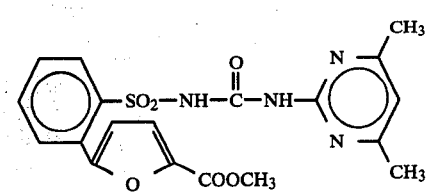
Compound 6
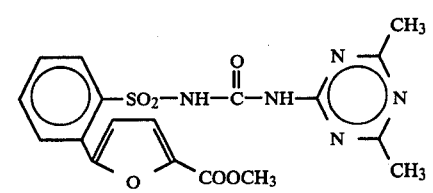
Compound 7
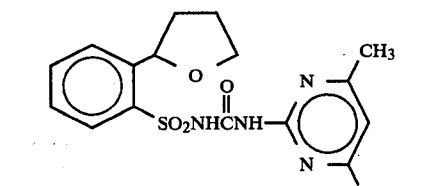
Compound 8
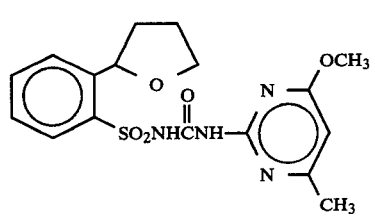
Compound 9
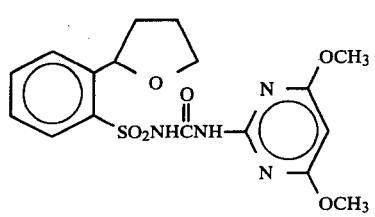
-continued
Compounds
Compound 10
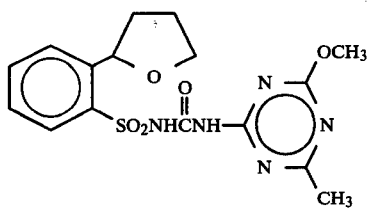
Compound 11
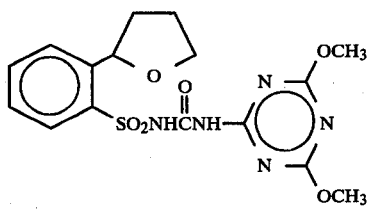
Compound 12
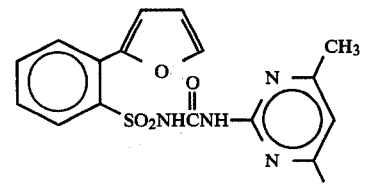
Compound 13
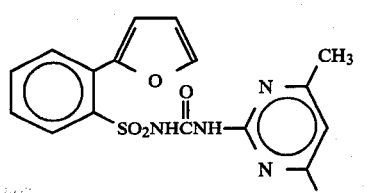
Compound 14
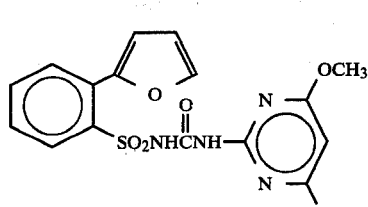
Compound 15
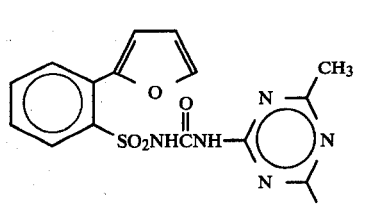
Compound 16
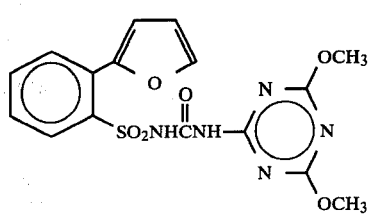

-continued
Compounds

Compound 17
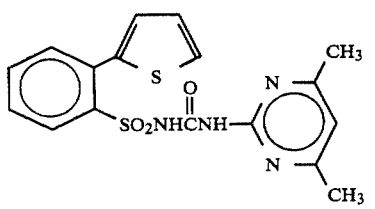

Compound 18
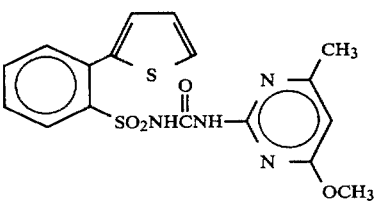

Compound 19
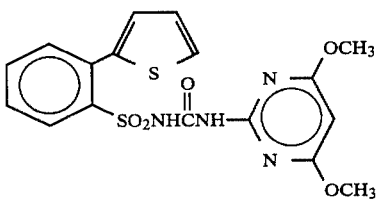

Compound 20
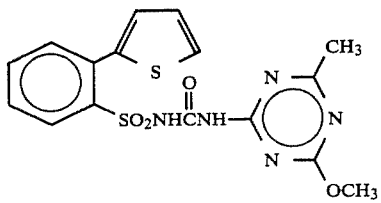

Compound 21
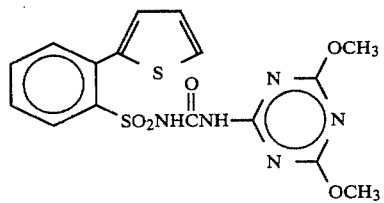

Test A

Seeds of crabgrass (Digitaria spp.), barnyardgrass (Echinochloa crusgalli), wild oats (Avena fatua), sicklepod (Cassia obtusifolia), morningglory (Ipomoea spp.), cocklebur (Xanthium spp.), sorghum, corn, soybean, rice, wheat and nutsedge tubers (Cyperus rotundus) were planted in a growth medium and treated pre-emergence with a nonphytotoxic solvent solution of the compounds of Table A. At the same time, cotton having five leaves (including cotyledonary ones), bush beans with the third trifoliolate leaf expanding, crabgrass with two leaves, barnyardgrass with two leaves, wild oats with two leaves, sicklepod with three leaves (including cotyledonary ones), morningglory with four leaves (including the cotyledonary ones), cocklebur with four leaves (including the cotyledonary ones), sorghum with four leaves, corn with four leaves, soybean with two cotyledonary leaves, rice with three leaves, wheat with one leaf, and nutsedge with three to five leaves were sprayed with a nonphytotoxic solvent solution of the compounds of Table A. Other containers of the above mentioned weeds and crops were treated pre- or post-emergence with the same nonphytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment. Several of the compounds tested were essentially innocuous to wheat but, at the same rate of application, provided effective weed control.

The following rating system was used:
0 = no effect;
10 = maximum effect;
C = chlorosis or necrosis;
E = emergence inhibition;
G = growth retardation;
H = formative effects;
S = albinism;
U = increased chlorophyl;
X = axillary stimulation; and
6Y = abscised buds or flowers.

The test data are summarized in Table A.

TABLE A

| Rate kg/ha | Cmpd. 1<br>2 | Cmpd. 2<br>2 | Cmpd. 3<br>2 | Cmpd. 4<br>2 | Cmpd. 5<br>2 | Cmpd. 6<br>2 | cmpd. 7<br>0.05 | cmpd. 8<br>0.05 |
|---|---|---|---|---|---|---|---|---|
| POST-EMERGENCE | | | | | | | | |
| Bush bean | 1H,5G | 4S,8G,6Y | 6C,9G,6Y | 6C,9G,6Y | 5C,9G,6Y | 1C,2G | 5C,9G,6Y | 6C,9G,6Y |
| Cotton | 5C,9G | 3C,3H,8G | 5C,9G | 5C,9G | 6C,9G | 2C,3H | 4C,9G | 5C,9G |
| Morningglory | 1C,4G | 1C | 3C,9G | 4C,9G | 2C,6G | 1C | 10C | 10C |
| Cocklebur | 3C,7H | 2C,7H | 5C,9G | 9C | 5C,9G | 3C,6H | 10C | 10C |
| Sicklepod | 2C | 2C | 4C | 4C | 1C,2G | 0 | 4C,6G | 4C,8G |
| Nutsedge | 2C,9G | 2C,5G,5X | 9G | 2C,9G | 1C,9G | 2G | 2C,8G | 2C,9G |
| Crabgrass | 6G | 2C | 2C,9G | 1C,2G | 2C,8G | 1C,3G | 2C,6G | 2C,9G |
| Barnyardgrass | 9H | 1C | 3C,9H | 2C,5H | 2C,8H | 0 | 5C,9H | 5C,9H |
| Wild Oats | 0 | 0 | 2C,8G,5X | 0 | 2C,6G | 0 | 4C,9G | 5C,9G |
| Wheat | 0 | 0 | 3C,9G | 2G | 3C,9G | 0 | 3U,9G | 4C,9G |
| Corn | 0 | 1C,3G | 2U,9G | 2C,9H | 2C,9G | 3C,7G | 5U,9G | 5U,9G |
| Soybean | 1C,3G | 1C,1H | 4C,8G | 4C,8G | 2C,4H | 2C,5G | 6C,9G | 5C,9G |
| Rice | 2C,9G | 0 | 5C,9G | 5G | 3C,9G | 2C,7G | 5C,9G | 5C,9G |
| Sorghum | 2C,7G | 1C,4G | 1C,9G | 3C,8H | 2C,9G | 2C,9G | 3C,9G | 5C,9H |
| Sugar beet | | | | | | | 3C,9H | 9C |
| PRE-EMERGENCE | | | | | | | | |
| Morningglory | 1C | 2C | 8G | 8G | 8G | 1C,3G | 5C,9G | 9G |
| Cocklebur | 8H | 9H | — | 9H | 9H | 9H | 9H | 9H |
| Sicklepod | 1C | 2C | 9C | 2C,7H | 1C,5G | 2C | 9G | 9G |

TABLE A-continued

| | | | | | | | | |
|---|---|---|---|---|---|---|---|---|
| Nutsedge | 9G | 10E | 10E | 10E | 10E | 9G | 9G | 10E |
| Crabgrass | 2C | 3C | 2C,6G | 2C | 3C | 0 | 2G | 3C,6G |
| Barnyardgrass | 5G | 3C | 3C,8H | 5C | 3C,6H | 3C | 2C,9H | 5C,9H |
| Wild Oats | 2G | 2G | 3C,9G | 1C,6G | 2C,9H | 2C,8G | 2C,9G | 5C,9G |
| Wheat | 2G | 2G | 3C,9G | 4G | 4C,9H | 5G | 2C,9G | 4C,9G |
| Corn | 2C,6G | 2C,8G | 9G | 2U,9G | 10E | 2C,8G | 9G | 4C,9G |
| Soybean | 0 | 1C,1H | 5H | 7H | 8H | 1C | 2C,5H | 9H |
| Rice | 3C,7H | 2C,3G | 10E | 2C,8G | 10E | 9H | 10E | 10E |
| Sorghum | 2C,7G | 2C,7G | 5C,9H | 2C,9H | 10E | 3C,9G | 5C,9H | 5C,9H |
| Sugar beet | | | | | | | 9G | 10E |

| | Cmpd. 9 | Cmpd. 10 | Cmpd. 11 | Cmpd. 12 | Cmpd. 13 | Cmpd. 14 | Cmpd. 15 | Cmpd. 16 |
|---|---|---|---|---|---|---|---|---|
| Rate kg/ha | 0.05 | 0.05 | 0.05 | 0.05 | 0.05 | 0.05 | 0.05 | 0.05 |
| POST-EMERGENCE | | | | | | | | |
| Bush bean | 5C,9G,6Y | 6C,9G,6Y | 5C,9G,6Y | 5C,9G,6Y | 6C,9G,6Y | 5C,9G,6Y | 5C,9G,6Y | 5C,9G,6Y |
| Cotton | 6C,9G | 4C,8G | 5C,9G | 0 | 2C,3G | 2C,5G | 3C,6G | 2C,5G |
| Sorghum | 4C,9G | 2C,9G | 9G | 2C,9G | 2C,9G | 9G | 1C,9G | 0 |
| Corn | 6U,9G | 2U,9G | 1U,9H | 2C,9G | 2C,9G | 2C,9G | 2C,9G | 0 |
| Soybean | 10C | 9C | 4C,8G | 5C,9H | 5C,9G | 9C | 9C | 9C |
| Wheat | 3C,9G | 2C,9G | 1C | 7G | 2C,7G | 0 | 1C,6G | 0 |
| Wild Oats | 4C,9G | 2C,9G | 1C,5G | 2C,9G | 2C,7G | 0 | 1C,6G | 0 |
| Rice | 6C,9G | 9C | 9C | 6C,9G | 5C,9G | 5C,9G | 6C,9G | 0 |
| Barnyardgrass | 5C,9H | 5C,9H | 2C,9H | 5C,9H | 5C,8H | 5C,9H | 2C,9H | 1H |
| Crabgrass | 4C,9G | 2C,8G | 1C,3G | 2C,9G | 2C,4G | 1C,6G | 2C,6G | 0 |
| Morningglory | 4C,7H | 5C,8H | 10C | 5G | 3C,5G | 2C,7G | 2C,8G | 5C,9G |
| Cocklebur | 10C | 10C | 10C | 2C,8H | 3C,9H | 3C,8H | 3C,8H | 4G |
| Sicklepod | 5C,9G | 3C,8H | 3C,5H | 2C,5G | 3C,6G | 3C,9H | 2C,6G | 2C,8H |
| Nutsedge | 5C,9G | 3C,8G | 3G | 2C,7G | 5G | 9G | 1C,8G | 5G |
| Sugar beet | 9C | 9C | 9C | 2C,7H | 10C | 5C,9G | 2C,9H | 4C,9G |
| PRE-EMERGENCE | | | | | | | | |
| Sorghum | 5C,9H | 5C,9H | 5C,9H | 3C,9H | 5C,9G | 5C,9H | 9H | 2G |
| Corn | 2C,9H | 2C,9G | 2C,9H | 3C,9G | 3C,9H | 2C,9G | 9G | 1C,6G |
| Soybean | 9H | 9H | 2C,5H | 5H | 8H | 8H | 9H | 8H |
| Wheat | 1C,9G | 2C,9G | 0 | 2C,9G | 2C,9G | 1C,6G | 2C,9G | 0 |
| Wild Oats | 3C,9G | 4C,9G | 5H | 3C,7G | 3C,8G | 1C,3G | 3C,8G | 2C |
| Rice | 10E | 10E | 10E | 2C,9H | 10E | 9H | 9H | 2G |
| Barnyardgrass | 5C,9H | 5C,9H | 2C,7H | 5C,9H | 5C,9H | 5C,9H | 5C,9H | 2C |
| Crabgrass | 2C,9G | 2C,8G | 0 | 2C | 2C,4G | 2C,6G | 4C,8G | 0 |
| Morningglory | 9G | 9C | 9C | 8G | 9G | 7G | 8G | 9G |
| Cocklebur | — | — | 9H | 9H | 9H | 9H | 9H | 9H |
| Sicklepod | 9G | 9G | 3C,9G | 9G | 8G | 9G | 9G | 8G |
| Nutsedge | 10E | 5C,9G | 0 | 2C,9G | 10E | 10E | 10E | 5G |
| Sugar beet | 10E | 10E | 10E | 9G | 10E | 10E | 10E | 10E |

| | Cmpd. 17 | Cmpd. 18 | Cmpd. 19 | Cmpd. 20 | Cmpd. 21 |
|---|---|---|---|---|---|
| Rate kg/ha | 0.05 | 0.05 | 0.05 | 0.05 | 0.05 |
| POST EMERGENCE | | | | | |
| Bush bean | 5C,8G,6Y | 5S,9G,6Y | 5C,9G,6Y | 9C | 9C |
| Cotton | 3C,5G | 4C,4H,8G | 6C,9G | 6C,9G | 3C,9G |
| Sorghum | 2C,8H | 3C,9H | 9H | 2G | 2C |
| Corn | 2C,6H | 3C,8H | 2C,9G | 2G | 0 |
| Soybean | 4C,9G | 3C,9G | 3C,9G | 5C,9G | 5C,9G |
| Wheat | 1H | 1C | 3G | 0 | 0 |
| Wild Oats | 1H | 2C | 3G | 0 | 0 |
| Rice | 2C,8G | 2C,8G | 2C,7G | 0 | 0 |
| Barnyardgrass | 2C,6H | 5C,9H | 9C | 2H | 0 |
| Crabgrass | 1C | 5G | 2C,4G | 0 | 2C |
| Morningglory | 5C,9G | 3C,8G | 5C,9H | 10C | 9C |
| Cocklebur | 2C,5G | 2C,8H | 5C,9G | 9C | 10C |
| Sicklepod | 3C | 2C,4G | 5C,8H | 4C,5G | 3C,4H |
| Nutsedge | 2C,6G | 3C,7G | 2C,8G | 5G | 0 |
| Sugar beet | — | — | — | — | — |
| PRE-EMERGENCE | | | | | |
| Sorghum | 4G | 3C,9H | 4C,9H | 2G | 0 |
| Corn | 3C,6G | 2C,8H | 9G | 1C,4G | 0 |
| Soybean | 1C | 3C,8H | 9H | 9H | 0 |
| Wheat | 5G | 8G | 7G | 0 | 0 |
| Wild Oats | 2C,4G | 2C,8G | 2C,8G | 0 | 0 |
| Rice | 0 | 3C,6G | 10E | 1C,4G | 0 |
| Barnyardgrass | 3G | 3C,9H | 3C,9H | 2G | 0 |
| Crabgrass | 3G | 2C,5G | 3C,8G | 2G | 2G |
| Morningglory | 5G | 8H | 9G | 9G | 8G |
| Cocklebur | 8H | 9H | 9H | 9H | 9H |
| Sicklepod | 8G | 9G | 9G | 9G | 9G |
| Nutsedge | 2G | 8G | 10E | 3G | 0 |
| Sugar beet | — | — | — | — | — |

Test B

Two plastic bulb pans were filled with fertilized and limed Fallsington slit loam or Woodstown sandy loam soil. One pan was planted with corn, sorghum, Kentucky bluegrass and several grass weeds. The other pan was planted with cotton, soybeans, purple nutsedge (*Cyperus rotundus*), and several broadleaf weeds. The following grassy and broadleaf weeds were planted: viously for Test A. The data are summarized in Table B.

TABLE 8

PRE-EMERGENCE ON FALLSINGTON SILT LOAM SOIL

| | Compound 3 | | Compound 7 | | Compound 8 | | Compound 9 | | Compound 10 | | Compound 11 | | Compound 12 | |
|---|---|---|---|---|---|---|---|---|---|---|---|---|---|---|
| Rate kg/ha | 0.03 | 0.12 | 0.12 | 0.03 | 0.12 | 0.03 | 0.12 | 0.03 | 0.12 | 0.03 | 0.12 | 0.03 | 0.06 | 0.015 |
| Crabgrass | 3G | 4G | 8G | 7G | 9G | 8G | 9G | 8G | 9G | 8G | 5G | 2G | 0 | 0 |
| Barnyardgrass | 4G,2C | 5G,3C | 9G,9C | 9G | 10C | 9G,9C | 9G,9C | 9G | 10C | 9G,9C | 8G,5C | 6G | 0 | 0 |
| Sorghum | 4G | 5G | 10C | 10C | 10C | 10C | 10C | 10C | 10C | 10C | 10C | 9G | 7G | 6G |
| Wild Oats | 0 | 3G | 9G | 9G | 9G | 9G | 9G | 9G | 9G | 9G | 8G | 7G | 4G | 2G |
| Johnsongrass | 6G | 5G | 9G | 9G | 9G | 9G | 9G | 9G | 9G | 9G | 8G | 8G | 4G | 2G |
| Dallisqrass | 3G | 3G | 9G | 9G | 9G | 9G | 9G | 9G | 9G | 9G | 6G | 3G | 2G | 0 |
| Giant foxtail | 4G | 4G | 8G | 2G | 10C | 8G | 10C | 9G | 9G | 7G | 4G | 2G | 0 | 0 |
| Ky. bluegrass | 3G | 6G | 10C | 9G | 10C | 9G | 10C | 9G | 10C | 9G | 4G | 2G | 6G | 4G |
| Cheatgrass | 0 | 3G | 10C | 10C | 10C | 10C | 10C | 10C | 10C | 10C | 8G | 5G | 7G | 5G |
| Sugar beets | 2G | 5G | 10C | 9G | 10C | 10C | 10C | 10C | 10C | 10C | 10C | 10C | 5G | 4G |
| Corn | 4G | 3G | 10C | 9G | 10C | 9G | 10C | 7G | 10C | 9G | 9G | 5G,3H | 0 | 0 |
| Mustard | 4G | 6G,5H | 10C | 10C | 10C | 10C | 10C | 10C | 10C | 10C | 10C | 10C | 9G | 8G |
| Cocklebur | 2G | 0 | 9G | 8G | 10C | 9G | 10C | 9G | 9G | 9G | 9G | 8G | 2G | 2G |
| Pigweed | 0 | 8G,9C | — | — | — | — | — | — | — | — | — | — | — | — |
| Nutsedge | 0 | 0 | 10C | 9G | 10C | 10C | 10C | 10C | 10C | 10C | 9G | 8G | 0 | 0 |
| Cotton | 0 | 2G | 9G | 8G | 9G | 9G | 9G | 9G | 9G | 9G | 9G | 8G | 2G | 2G |
| Morningglory | 0 | 0 | 9G | 8G | 9G | 9G | 9G | 8G | 9G | 9G | 9G | 8G | 3G | 0 |
| Sicklepod | 0 | 3G | 9G | 8G | 9G | 9G | 9G | 9G | 9G | 9G | 9G | 8G | 0 | 0 |
| Teaweed | 0 | 3G | 9G | 9G | 9G | 9G | 9G | 9G | 9G | 9G | 9G | 8G | 0 | 0 |
| Velvetleaf | 0 | 3G | 9G | 9G | 9G | 9G | 9G | 9G | 9G | 9G | 9G | 8G | 0 | 0 |
| Jimsonweed | 0 | 2G | 9G | 9G | 9G,9C | 9G | 9G,9C | 9G | 9G,9C | 9G | 9G | 8G | 2G | 0 |
| Soybean | 3G | 5G | 8G,7H | 6G,5H | 9G | 9G | 9G | 9G | 9G | 9G | 7G,7H | 2G,2C | 0 | 0 |
| Rice | 6G | 7G | 10C | 10C | 10C | 10C | 10C | 10C | 10C | 10C | 10C | 10C | 9G | 7G |
| Wheat | 2G | 4G | 10C | 8G | 10C | 9G | 7G | 4G | 9G | 8G | 4G | 2G | 5G | 5G |

| | Compound 13 | | Compound 14 | | Compound 15 | | Compound 16 | |
|---|---|---|---|---|---|---|---|---|
| Rate kg/ha | 0.06 | 0.015 | 0.06 | 0.015 | 0.06 | 0.015 | 0.12 | 0.03 |
| Crabgrass | 2G | 0 | 3G | 0 | 5G | 2G | 0 | 0 |
| Barnyardgrass | 7G | 4G | 3G | 5G | 6G | 4G | 5G | 3G |
| Sorghum | 9G | 4G | 10C | 2G | 9G | 7G | 4G | 2G |
| Wild Oats | 6G | 0 | 3G | 2G | 5G | 4G | 4G | 2G |
| Johnsongrass | 8G | 2G | 3G | 2G | 3G | 2G | 2G | 0 |
| Dallisqrass | 2G | 0 | 2G | 0 | 6G | 2G | 5G | 2G |
| Giant foxtail | 8G | 0 | 2G | 2G | 3G | 0 | 0 | 0 |
| Ky. bluegrass | 7G | 3G | 6G | 3G | 9G | 7G | 3G | 3G |
| Cheatgrass | 8G | 4G | 9G | 8G | 8G | 7G | 5G | 4G |
| Sugar beets | 7G | 3G | 5G | 4G | 6G | 4G | 10C | 9G |
| Corn | 7G,7H | 3G | 4G | 3G | 5G | 4G | 4G | 3G |
| Mustard | 10C | 9G | 10C | 9G | 9C,9G | 9G | 10C | 9G,9C |
| Cocklebur | 2G | 0 | 0 | 0 | 4G | 0 | 7G | 5G |
| Pigweed | — | — | — | — | — | — | — | — |
| Nutsedge | 4G | 2G | 3G | 2G | 3G | 2G | 7G | 5G |
| Cotton | 4G | 0 | 2G | 0 | 3G | 2G | 7G | 4G |
| Morningglory | 3G | 3G | 4G | 3G | 4G | 4G | 8G | 5G |
| Sicklepod | 4G | 4G | 7G | 2G | 2G | 0 | 9G | 8G |
| Teaweed | 6G | 0 | 0 | | 2G | 0 | 3G | 0 |
| Velvetleaf | 6G | 0 | 0 | 0 | 5G | 2G | 2G | 0 |
| Jimsonweed | 7G | 0 | 5G | 4G | 4G | 3G | 5G | 4G |
| Soybean | 6G,5H | 0 | 2G | 0 | 2G | 2G | 6G,5H | 5G,3H |
| Rice | 9G | 7G | 8G | 8G | 8G | 8G | 6G | 6G |
| Wheat | 6G | 6G | 3G | 3G | 5G | 3G | 2G | 2G | crabgrass (*Digitaria sanguinalis*) barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), sicklepod (*Cassia obtusifolia*) teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described pre- Test C The test chemicals, dissolved in a non-phytotoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table C.

All plant species were seeded in Woodstown sandy loam or Fallsington silt loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipo-*

*moea hederacea*), jimsonweed (*Datura stramonium*) cocklebur (*Xanthium pensylvanicum*), crabgrass (*Digitaria sp.*), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugar beets, and rape. All plants were sprayed approximately 14 days after planting. Additional plant species such as johnsongrass and bindweed, are sometimes added to this standard test in order to evaluate unusual selectivity.

Compound Nos. 20 and 21 exhibit selectivity in post-emergence control of weeds in corn and wheat.

TABLE C

Over-the-Top Soil/Foliage Treatment

| | Compound 3 | | Compound 5 | | Compound 7 | | | Compound 8 | | | Compound 9 | | |
|---|---|---|---|---|---|---|---|---|---|---|---|---|---|
| Rate kg/ha | 0.06 | 0.25 | 0.06 | 0.25 | 0.06 | 0.015 | 0.004 | 0.06 | 0.015 | 0.004 | 0.06 | 0.015 | 0.004 |
| Soybeans | 3G,2C | 5G,2C | 6G,2C | 9G,5C | 10C | 7G,2C | 2G | 8G,6C | 6C,7G | 6G,6C | 10C | 9C | 8G,7C |
| Velvetleaf | 0 | 6G,1C | 0 | 4G | 7G,4C | 6G | 3G | 9G | 4C,6G | 2C,7G | 10C | 9C | 9C |
| Sesbania | 4G | 5G | 6G,2C | 6G,2C | 10C | 10C | 7G | 9C | 10C | 9C | 10C | 10C | 8G |
| Sicklepod | 1C | 2C | 5G | 0 | 8G | 6G | 2G | 6G | 3G | 2G | 4G | 5G | 8G |
| Cotton | 6G,3C | 8G,5C | 1G | 5G,1C | 8G | 6G | 3G | 10C | 9G | 9G | 10C | 9G | 9G |
| Morningglory | 1G,2C | 3G,2C | 2C | 4G,2C | — | — | — | 5G,3C | 3G,2C | 4G,2C | 3C,8G | 1G,1C | 4C,4G |
| Alfalfa | 0 | 1G | 0 | 2G | | | | | | | | | |
| Jimsonweed | 1C | — | 0 | 1C | 8G | 6G | 4G | 7C,8G | 8G,7C | 7G | 8G | 9G | 6G |
| Cocklebur | 6G,2C | 5G,2C | 10G,2C | 10G,5C | 8G | 6G | 3G | 8G | 9G | 7G | 9G | 7G | 10C |
| Corn | 3G | 5G,3C | 8G,5H | 6G,5H | 7G,9C | 5C,7G | 2G | 7G,8C | 4G,4C | 3G,1C | 3C,5G | 4G,1C | 4G,3H |
| Crabgrass | 1G | 1G | 0 | 0 | 7G | 5G | 8G | 9G | 7G | 1G | 7G | 3G | 0 |
| Rice | 5G | 7G | 6G | 5G | 8G,2C | 7G | 4G | 6G,4C | 4C,4G | 4G | 6C,4G | 5G,5C | 3G |
| Nutsedge | 4G | 8G,4C | 7G,3C | 0 | 3G | 2G | — | 10C | 8C | 3G | 8G,8C | 7G,8C | 6G,4C |
| Barnyardgrass | 7G,2C | 6G,1C | 2C | 1C | 6G | 1C,2G | 1G | 7G | 4G | 5G | 6G,4C | 5G,5C | 6G |
| Wheat | 1G | 1G | 6G | 2C | 9G | 7G | 5G | 8G | 5G | 4G | 5G | 4G | 3G |
| Giant foxtail | 7G | 5G | 1G | 0 | — | — | — | 9G | 7G | 1G | 8G | 7G | 4G |
| Wild Oats | 4G | 5G | 4G | 3G | 8G | 7G | — | 6G | 6G | 2G | 8G | 7G | 1G |
| Sorghum | 7G,1C | 7G,1C | 7G | 5G,4C | 7G | 7G | 6G | 6G | 5G | 4G | 10C | 7G,7C | 7G |
| Sunflower | | | | | 10C | 2C,8G | 3G | 10C | 10C | 10C | 10C | 10C | 10C |
| Rape | | | | | 5C,4G | 2C,3G | 1C,3G | 9G | 8G | 6G,3C | 10C | 9C | 7G |
| Johnsongrass | | | | | 9G | 7G | 9G | 10C | 7C,8G | 7G | 10C | 8G,7C | 7G,7C |
| Sugar beets | | | | | 9C | 6G | 2C,3G | 5G | 10C | 8C | 5C | 4G | 3G |
| Bindweed | | | | | 5G | 2G | 1C | 2G | 0 | 0 | 0 | 0 | 0 |

| | Compound 11 | | Compound 12 | | Compound 13 | | Compound 14 | | Compound 15 | | Compound 16 | |
|---|---|---|---|---|---|---|---|---|---|---|---|---|
| Rate kg/ha | 0.06 | 0.015 | 0.06 | 0.015 | 0.06 | 0.015 | 0.06 | 0.015 | 0.06 | 0.015 | 0.06 | 0.015 |
| Soybeans | 10C | 9C | 8C,4G | 7G,2C | 8C,7G | 8C | 9C | 8G | 10C | 10C | 10C | 9C |
| Velvetleaf | 8G | 7G | 7G | 3G | 3G | 1C,2G | 4G | 3G | 8G | 3G | 6G | 2G |
| Sesbania | 8G,9C | 8G,7C | 8G,4C | 7C,3G | 8G,4C | 1C,7G | 10C | 7G | 10C | 8G | 10C | 10C |
| Sicklepod | 6G | 4G | 8G | 6G | 2C,5G | 8G | 5G | 2G | 8G | 4G | 8G | 5G |
| Cotton | 9G,9C | — | 7G | — | 8G | 7G,4C | 8G | 6G | 4G,7C | 6G | 8G | 3G |
| Morningglory | 9G | 9G,8C | — | 3G | 9G | 9G | 9C | 4G | 8G | 5G | 4G,1C | 1G |
| Jimsonweed | 9G | 8G | 8G | 9G | — | 9G | — | — | 4G,3C | 8G | 9G | 6G |
| Cocklebur | 10C | 9G | 7G | — | 7G,2C | 7G | 9C | 3G | 10C | 7G | 7G | 2G |
| Corn | 8G | 6G,4C | 7G | 4G | 5C,6G | 7G | 10C | 7G,5C | 7G,4C | 6G | 1H,4G | 1G |
| Crabgrass | 2G | 0 | 5G | 0 | 6G | 1G | 7G | 7G | 5G | 2G | 3G | 1G |
| Rice | 6G,4C | 4G | 5G,4C | 6G,3C | 4G | 3G | 6G,4C | 4G | 6G,5C | 4G,3C | 2G | 0 |
| Nutsedge | 0 | 0 | 3G | 0 | 0 | 0 | 5G | 4G | 4G,3C | 3G,3C | 0 | 0 |
| Barnyardgrass | 6G | 5G,3C | 9G,7C | 7G,4C | 10C | 7C,6G | 10C | 10C | 9G | 8G | 3G | 1G |
| Wheat | 5G | 5G | 7G | 4G | 5G | 4G | 5G | 4G | 8G | 2G | 4G,1C | 1G |
| Giant foxtail | 4G | 0 | 6G | 5G | 3C,4G | 3G | 8G | 5G | 3C,8G | 6G,1C | 2G | 0 |
| Wild Oats | 7G | 5G | 8G | 3G | 9G | 8G | 6G | 6G | 3G | 2G | 3G,2G | 2C,1G |
| Sorghum | 8G | 8G | 8G | 8G | 8G | 9G | 8G | 8G | 8G | 8G | 4G | 1G |
| Sunflower | 10C | 10C | 8G | 2G | 10C | 2C,6G | 10C | 8G | 10C | — | 7G | 5G |
| Rape | 9G | 8G | 8G | 7G | 9G | 8G | 6G | 7G | 8G | 7G | 10C | 10C |
| Johnsongrass | 1G | 0 | 7C,8G | 2G | 5G,4C | 1G | 7G | 4G | 9G | 2G | 0 | 0 |
| Sugar beets | 7C,8G | 8G,5C | 6G | 5G | 7G | 8C | 6G | 10C | 6G | 3G | 6C,5G | 4G |
| Bindweed | 4G | 3G | 6G | 2G | 0 | 0 | 2G | 0 | 5G | 2G | 0 | 0 |

| | Compound 17 | | | Compound 18 | | | Compound 19 | | Compound 20 | | Compound 21 | |
|---|---|---|---|---|---|---|---|---|---|---|---|---|
| Rate kg/ha | 0.06 | 0.015 | 0.004 | 0.06 | 0.015 | 0.004 | 0.015 | 0.004 | 0.06 | 0.015 | 0.06 | 0.015 |
| Soybeans | 9C | 6C,6G | 3C | 7C,6G | 8C | 5G,7C | 9C | 4G,5C | 9C | 10C | 10C | 10C |
| Velvetleaf | 4G | 3G | 4G | 5G | 3C,6G | 3G | 3G | 3G | 3G | 3G | 3G | 2G |
| Sesbania | 4C,5G | 4G | 3G | 9G | 7G | 3G | 7C,6G | 7G,4C | 10C | 10C | 10C | 10C |
| Sicklepod | 9G | 6G | 4G | 6G | 3G | 2G | 2G | 0 | 8G | — | 8G | 6G |
| Cotton | 8G | 7G | 3G | 9C | 8G | 6G | 5G | 4G | 8G | 8G | 9C | 7G |
| Morningglory | 7G | 3G | 0 | 8G | 9C | 5G | 3G | 0 | 10C | 10C | 9C | 2C,4G |
| Jimsonweed | 0 | 0 | 0 | 9G | 4G | 3G | 6G | 1G | 7G | 4G | 6G | 4G |
| Cocklebur | 8G | 3G | 4G | 3G | 5G | 4G | 2G | 1G | 10C | 10C | 9G | 4G |
| Corn | 0 | 0 | 0 | 4H,5G | 4G | 0 | 0 | 0 | 0 | 0 | 0 | 0 |
| Crabgrass | 0 | 0 | 0 | 1G | 0 | 0 | 2G | 0 | 0 | 1G | 0 | 0 |
| Rice | 3G | 0 | 2G | 0 | 0 | 0 | 0 | 0 | 0 | 0 | 2G | 0 |
| Nutsedge | 0 | 0 | 0 | 0 | 0 | 0 | 3C | 0 | 0 | 0 | 0 | 0 |
| Barnyardgrass | 0 | 0 | 0 | 2G | 3G | 0 | 0 | 0 | 0 | 0 | 0 | 0 |
| Wheat | 0 | 0 | 0 | 1G | 0 | 0 | 0 | 0 | 0 | 0 | 1G | 0 |
| Giant foxtail | 0 | 0 | 0 | 2G | 0 | 0 | 0 | 0 | 0 | 0 | 1G | 0 |
| Wild Oats | 0 | 0 | 0 | 1G | 1G | 0 | 0 | 0 | 1G | 0 | 0 | 0 |
| Sorghum | 2G | 0 | 0 | 7G | 4G | 0 | 5G | 2G | 0 | 0 | 0 | 0 |
| Sunflower | 5G | 3G | 4G | 3G | 5G | 3G | 3G | 2G | 10C | 10C | 9G | 9G |

TABLE C-continued

| | Over-the-Top Soil/Foliage Treatment | | | | | | | | | | | |
|---|---|---|---|---|---|---|---|---|---|---|---|---|
| Rape | 6G | 5G | 5G | 8G | 6G | 4G | 9C | 9G | 10C | 10C | 10C | 7G,9C |
| Johnsongrass | 0 | 0 | 0 | 1G | 0 | 0 | 0 | 0 | 0 | 0 | 2G | 0 |
| Sugar beets | 2G | 0 | 0 | 9G | 3G | 9G | 4G | 0 | 10C | 10C | 8G | 5G |
| Bindweed | 4G | 0 | 0 | 3G | 3G | 0 | 8G | 2G | 4G | 0 | 0 | 0 |

Test D

Two plastic pans lined with polyethylene liners were filled with prepared Woodstown sandy loam soil. One pan was planted with seeds of wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), Italian ryegrass (*Lolium multiflorum*) and rapeseed (*Brassica napus*). The other pan was planted with seeds of Russian thistle (*Salsola kali*), cleavers (*Galium aparine*), speedwell (*Veronic persica*), kochia (*Kochia scoparia*), shepherd's purse (*Capsella bursa-pastoris*), Matricaria inodora, black nightshade (*Solanum nigrum*), wild buckwheat (*Polygonum convolvulus*) and sugar beets (*Beta vulgaris*). Species which sometimes are included in this test are tansy mustard (*Descurainia pinnata*), tumble mustard (*Sisymbrium altissium*), ripgut brome (*Bromus rigidus*), quackgrass (*Agropyron repens*), downy brome (*Bromus tectorum*) and yellow rocket (*Barbarea vulgaris*). The above two pans were treated pre-emergence. At the same time two pans in which the above plant species were already growing were treated post-emergence. Plant heights at the time of treatment ranged from 1–20 cm depending on plant species.

The compounds applied were diluted with a non-phytotoxic solvent and sprayed over-the-top of the pans. An untreated control and a solvent alone control were included for comparison. All treatments were maintained in the greenhouse for 19–22 days at which time the treatments were compared to the controls and the effects visually rated. The recorded data are presented in Table D. Some of the compounds tested exhibit selectivity while controlling weeds in cereal crops, such as wheat and barley.

TABLE D

| | Compound 9 | | | |
|---|---|---|---|---|
| | Pre-Emergence | | Post-Emergence | |
| Rate kg/ha | 0.015 | 0.004 | 0.015 | 0.004 |
| wheat | 5G | 2G | 5G | 5G |
| barley | 9G | 7G | 9G | 5G |
| wild oats | 7G | 6G | 6G | 4G |
| cheatgrass | 9G | 8G | 7G | 8G |
| blackgrass | 8C,9G | 8G | 10C | 8C,9G |
| annual bluegrass | 4C,9G | 8G | 10C | 10C |
| green foxtail | 8G | 0 | 9G | 8G |
| Italian ryegrass | 8G | 7G | 3C,8G | 7G |
| rapeseed | 10C | 9G | 10C | 10C |
| ripgut brome | — | — | — | — |
| *Matricaria inodora* | 9G | 9G | 10C | 10C |
| Galium aparine | 8G | 8G | 10C | 10C |
| Russian thistle | 0 | 3G | 10C | 8C |
| sheperd's purse | 10E | 10E | 10C | 10C |
| kochia | 8G | 8G | 9C,9G | 9C,9G |
| black nightshade | 7G | 5G | 7G | 5G |
| speedwell | 4G | 3G | 3G | 0 |
| wild buckwheat | 4G | 6G | 10C | 3G,8C |
| sugar beets | 8G | 8G | 10C | 10C |
| tansy mustard | — | — | — | — |
| tumble mustard | — | — | — | — |

| | Compound 11 | |
|---|---|---|
| | Pre-Emergence | Post-Emergence |

TABLE D-continued

| Rate kg/ha | 0.06 | 0.015 | 0.06 | 0.015 |
|---|---|---|---|---|
| wheat | 1G | 0 | 2G | 0 |
| barley | 4G | 0 | 2G | 0 |
| wild oats | 2G,8G | 5G | 6G | 2G |
| cheatgrass | 6G | 0 | 0 | 0 |
| blackgrass | 2C,8G | 6G | 8G | 2C,5G |
| annual bluegrass | 8G | 7G | 8G | 4G |
| green foxtail | 3G | 3G | 3G | 3G |
| Italian ryegrass | 2C,8G | 6G | 5G | 0 |
| rapeseed | 9G | 9G | 9G | — |
| ripgut brome | 8G | 6G | 7G | 0 |
| *Matricaria inodora* | 7C,9G | 7G | 6G | 0 |
| Galium aparine | 3C,9G | 7G | 6G | — |
| Russian thistle | 2C,8G | 3G | 0 | 0 |
| sheperd's purse | 9C,9G | 8G | 6G | — |
| kochia | 8G | 0 | 0 | 0 |
| black nightshade | 6G | 4G | 2G | — |
| speedwell | 7G | 2G | — | — |
| wild buckwheat | 2C,8G | 6G | 0 | — |
| sugar beets | — | — | — | — |
| tansy mustard | 5C,9G | 9G | 8G | — |
| tumble mustard | 9C,9G | 7G | 0 | 0 |

| | Compound 11 | | | |
|---|---|---|---|---|
| | Pre-Emergence | | Post-Emergence | |
| Rate kg/ha | 0.015 | 0.004 | 0.015 | 0.004 |
| wheat | 0 | 0 | 0 | 0 |
| barley | 0 | 0 | 0 | 0 |
| wild oats | 0 | 0 | 0 | 0 |
| cheatgrass | 0 | 0 | 0 | 0 |
| blackgrass | 5G | 4G | 5G | 0 |
| annual bluegrass | 6G | 4G | 4G | 0 |
| green foxtail | 3G | 2G | 3G | 0 |
| Italian ryegrass | 1C,5G | 3G | 2G | 0 |
| rapeseed | 9G | 9G | 10C | 8G |
| ripgut brome | — | — | — | — |
| *Matricaria inodora* | 9G | 5G | 9C,9G | 8C,8G |
| Galium aparine | 7G | 2G | 10C | 9C,9G |
| Russian thistle | 2G | 0 | 0 | 0 |
| sheperd's purse | 10C | 7G | 10C | 10C |
| kochia | 5G | 0 | 5G | 0 |
| black nightshade | 6G | 2G | 5G | 0 |
| speedwell | 2G | 2G | 0 | 0 |
| wild buckwheat | 2C,9G | 7G | 7G | 3G |
| sugar beets | 10C | 9G | 10C | 8G |
| tansy mustard | — | — | — | — |
| tumble mustard | — | — | — | — |

| | Compound 14 | | | |
|---|---|---|---|---|
| | Pre-Emergence | | Post-Emergence | |
| Rate kg/ha | 0.015 | 0.06 | 0.015 | 0.06 |
| wheat | 2G | 4G | 2G | 2G |
| barley | 2G | 5G | 3G | 4G |
| wild oats | 3G | 5G | 2G | 2G |
| downy brome | — | — | — | — |
| cheatgrass | 3G | 6G | 2G | 4G |
| blackgrass | 6G | 8G | 4G | 6G |
| annual bluegrass | 6G | 2C,8G | 5G | 6G |
| green foxtail | 0 | 5G | 6G | 3G |
| quackgrass | — | — | — | — |
| Italian ryegrass | 5G | 2C,7G | 2G | 4G |
| ripgut brome | — | — | — | — |
| Russian thistle | 2C,2G | 2C,3G | 0 | 2C |
| tansy mustard | — | — | 6G | 2C,8G |
| Galium aparine | — | — | 0 | 2C,4G |
| tumble mustard | 10C | 9G | 4G | 10C |
| kochia | 6G | 8G | 0 | 7C |
| shepherd's purse | 9G | 9C,9G | 4G | 3C,8G |
| *Matricaria inodora* | 9G | 9G | 3G | 3C,8G |
| black nightshade | 3G | 6G | 0 | 5G |
| yellow rocket | 9G | 9G | 0 | 3G |

TABLE D-continued

| | | | | |
|---|---|---|---|---|
| rapeseed | 8G | 9C,9G | 7G | 10C |
| wild buckwheat | 7G | 7G | 0 | 2G |
| Veronica persica | 7C,9G | 10C | — | — |

Compound 15

| | Pre-Emergence | | Post-Emergence | |
|---|---|---|---|---|
| Rate kg/ha | 0.015 | 0.06 | 0.015 | 0.06 |
| wheat | 6G | 7G | 2G | 5G |
| barley | 6G | 7G | 2G | 6G |
| wild oats | 5G | 7G | 2G | 4G |
| downy brome | — | — | — | — |
| cheatgrass | 2C,8G | 10C | 0 | 6G |
| blackgrass | 2C,8G | 3C,8G | 4G | 2C,8G |
| annual bluegrass | 2C,9G | 3C,9G | 6G | 2C,8G |
| green foxtail | 6G | 2C,9G | 5G | 7G |
| quackgrass | — | — | — | — |
| Italian ryegrass | 2C,9G | 2C,9G | 3G | 5G |
| ripgut brome | — | — | — | — |
| Russian thistle | 2C,5G | 2C,6G | 0 | 2G |
| tansy mustard | — | — | 4G | 8C |
| Galium aparine | 5G | — | 2G | 0 |
| tumble mustard | 10C | 10C | 4G | 10C |
| kochia | 6G | 10C | 0 | 7G |
| sheperd's purse | 9G | 10C | 3G | 2C,8G |
| Matricaria inodora | 9G | 9G | 2G | 6G |
| black nightshade | 3G | 6G | 0 | 0 |
| yellow rocket | 9G | 9G | 4G | 6G |
| rapeseed | 9C | 10C | 5G | 8G |
| wild buckwheat | 7G | 7G | 5G | 7G |
| Veronica persica | 9G | 9C,9G | — | — |

Compound 20

| | Pre-Emergence | | Post-Emergence | |
|---|---|---|---|---|
| Rate kg/ha | 0.06 | 0.015 | 0.06 | 0.015 |
| wheat | 0 | 0 | 0 | 0 |
| barley | 2G | 0 | 0 | 0 |
| wild oats | 3G | 0 | 0 | 0 |
| downy brome | 4G | 0 | 0 | 0 |
| cheatgrass | 0 | 0 | 0 | 0 |
| blackgrass | 4G | 4G | 0 | 0 |
| annual bluegrass | 4G | 3G | 2G | 0 |
| green foxtail | 2G | 0 | 3G | 0 |
| quackgrass | 3G | 0 | 0 | 0 |
| Italian ryegrass | 4G | 3G | 0 | 0 |
| ripgut brome | 2G | 0 | 0 | 0 |
| Russian thistle | 0 | 0 | 0 | 0 |
| tansy mustard | 10C | 9G | 10C | 10C |
| Galium aparine | 5G | 5G | 3G | 4G |
| tumble mustard | 9G | 8G | 10C | 8G |
| kochia | 8G | 6G | 0 | 0 |
| shepherd's purse | 10C | 9G | 10C | 10C |
| Matricaria inodora | 9G | 9G | 9C | 8C |
| black nightshade | 5G | 5G | 0 | 0 |
| yellow rocket | 9G | 8G | 10C | 10C |
| rapeseed | 9G | 7G | 10C | 10C |
| wild buckwheat | 5G | 7G | 6G | 3G |

What is claimed is:

1. A compound of the formula:

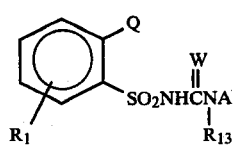

where Q is

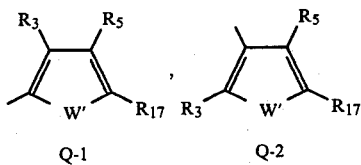

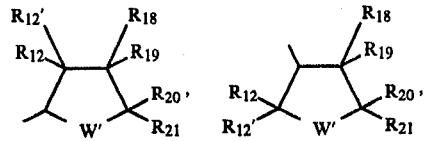

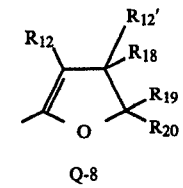

where
W is O or S;
W' is O or S;
$R_1$ is H, F, Cl, Br, $CH_3$, $CF_3$ or $OCH_3$;
$R_3$ is H, $CH_3$, $C_2H_5$, Cl, Br, $OCH_3$ or $OC_2H_5$;
$R_5$ is H, $CH_3$, $C_2H_5$, Cl, Br, $OCH_3$ or $OC_2H_5$;
$R_{17}$ is H, $CH_3$, $C_2H_5$, Cl, Br, $OCH_3$, $OC_2H_5$ or $CO_2CH_3$;
$R_{12}$ is H or $CH_3$;
$R_{12}'$ is H or $CH_3$;
$R_{13}$ is H or $CH_3$;
$R_{18}$ is H or $CH_3$;
$R_{19}$ is H or $CH_3$;
$R_{20}$ is H or $CH_3$;
$R_{21}$ is H or $CH_3$;

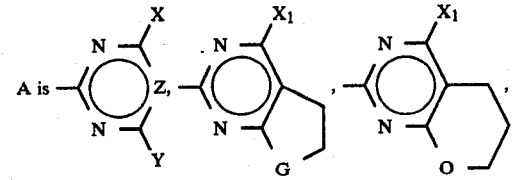

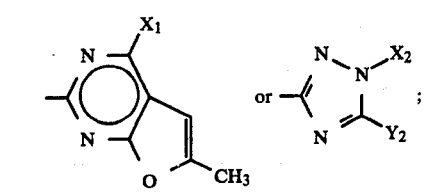

X is $CH_3$, $OCH_3$ or Cl;
Y is $CH_3$, $C_2H_5$, $CH_2OCH_3$, $OCH_3$, $OC_2H_5$, $CH(OCH_3)_2$, $SCH_3$, $CF_3$, $NH_2$, $NHCH_3$, $N(CH_3)_2$, $OCH_2CH_2OCH_3$, $OCH_2CF_3$ or

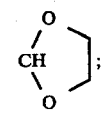

Z is CH;
$X_1$ is $CH_3$, $OCH_3$ or Cl;
G is O or $CH_2$;
$X_2$ is $C_1$–$C_3$ alkyl or $CH_2CF_3$;
$Y_2$ is $CH_3O$, $C_2H_5O$, $CH_3S$ or $C_2H_5S$;
and their agriculturally suitable salts; provided that
(1) when W is S, then $R_{13}$ is H, A is 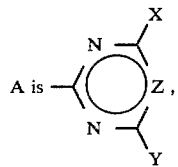

Y is $CH_3$, $OCH_3$, $C_2H_5$, $CH_2OCH_3$, $CH(OCH_3)_2$ or

;

(2) when Q is

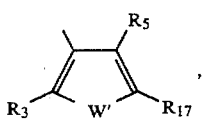, then $R_3$ is H, $CH_3$ or $C_2H_5$; $R_5$ is H, $CH_3$ or $C_2H_5$; and $R_{17}$ is H, $CH_3$, $C_2H_5$ or $-CO_2CH_3$;

(3) when one of $R_3$, $R_5$, $R_{17}$ is other than H, then the other two substituents are H or $CH_3$;

(4) the total number of carbon atoms in $R_{12}$, $R_{12}'$, $R_{18}$, $R_{19}$, $R_{20}$, and $R_{21}$ is less than or equal to 4;

(5) when X is Cl, then Y is $OCH_3$, $NH_2$, $OC_2H_5$, $NHCH_3$ or $N(CH_3)_2$.

2. Compounds of claim 1 where W is O.

3. Compounds of claim 2 where $R_1$ and $R_{13}$ are H.

4. Compounds of claim 3 where $R_3$ is H, $CH_3$ or $C_2H_5$; $R_5$ is H, $CH_3$ or $C_2H_5$; and $R_{17}$ is H, $CH_3$, $C_2H_5$ or $-CO_2CH_3$.

5. Compounds of claim 4 where Y is $CH_3$, $OCH_2OCH_3$, $OCH_3$, $OC_2H_5$, $CH(OCH_3)_2$ or

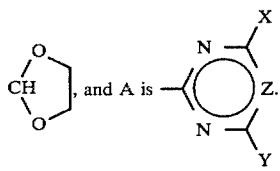

6. Compounds of claim 5 where Q is

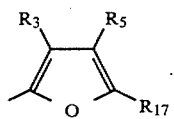

7. Compounds of claim 5 where Q is

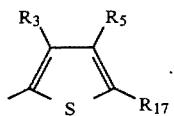

8. Compounds of claim 5 where Q is

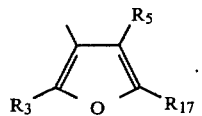

9. Compounds of claim 5 where Q is

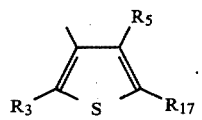

10. Compounds of claim 5 where Q is

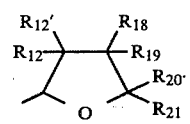

11. Compounds of claim 5 where Q is

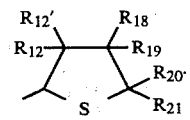

12. Compounds of claim 5 where Q is

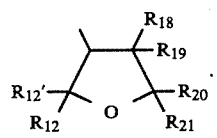

13. Compounds of claim 5 where Q is

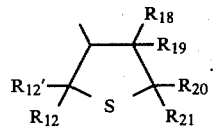

14. Compounds of claim 5 where Q is

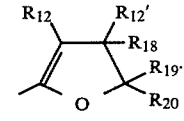

15. The compound of claim 1 which is N-[(4,6-dimethylpyrimidin-2-yl)aminocarbonyl]-2-(tetrahydrofuran-2-yl)benzenesulfonamide.

16. The compound of claim 1 which is N-[(4-methoxy-6-methylpyrimidin-2-yl)aminocarbonyl]-2-(tetrahydrofuran-2-yl)benzenesulfonamide.

17. The compound of claim 1 which is N-[(4,6-dimethoxypyrimidin-2-yl)aminocarbonyl]-2-(tetrahydrofuran-2-yl)benzenesulfonamide.

18. The compound of claim 1 which is N-[(4-chloro-6-methoxypyrimidin-2-yl)aminocarbonyl]-2-(tetrahydrofuran-2-yl)benzenesulfonamide.

19. A composition suitable for controlling the growth of undesired vegetation which comprises an effective amount of a compound of claim 1 and at least one of the following: surfactant, solid or liquid inert diluent.

20. A composition suitable for controlling the growth of undesired vegetation which comprises an effective amount of a compound of claim 2 and at least one of the following: surfactant, solid or liquid inert diluent.

21. A composition suitable for controlling the growth of undesired vegetation which comprises an effective amount of a compound of claim 3 and at least one of the following: surfactant, solid or liquid inert diluent.

22. A composition suitable for controlling the growth of undesired vegetation which comprises an effective amount of a compound of claim 4 and at least one of the following: surfactant, solid or liquid inert diluent.

23. A composition suitable for controlling the growth of undesired vegetation which comprises an effective amount of a compound of claim 5 and at least one of the following: surfactant, solid or liquid inert diluent.

24. A method for controlling the growth of undesired vegetation which comprises applying to the locus to be protected an effective amount of a compound of claim 1.

25. A method for controlling the growth of undesired vegetation which comprises applying to the locus to be protected an effective amount of a compound of claim 2.

26. A method for controlling the growth of undesired vegetation which comprises applying to the locus to be protected an effective amount of a compound of claim 3.

27. A method for controlling the growth of undesired vegetation which comprises applying to the locus to be protected an effective amount of a compound of claim 4.

28. A method for controlling the growth of undesired vegetation which comprises applying to the locus to be protected an effective amount of a compound of claim 5.

* * * * *